(12) United States Patent
Kear

(10) Patent No.: US 7,883,515 B2
(45) Date of Patent: Feb. 8, 2011

(54) MEDICAL DEVICE

(75) Inventor: Jason W. Kear, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/394,407

(22) Filed: Feb. 27, 2009

(65) Prior Publication Data

US 2009/0198250 A1 Aug. 6, 2009

Related U.S. Application Data

(62) Division of application No. 10/202,978, filed on Jul. 25, 2002, now abandoned.

(51) Int. Cl.
 *A61B 17/22* (2006.01)
(52) U.S. Cl. .................................................. 606/127
(58) Field of Classification Search ............... 606/108, 606/110, 115, 123, 127, 128, 159, 111–114; 604/19, 27, 35–38, 41, 48, 118, 119, 313–316, 604/540–544, 902, 22; 433/91, 93
 See application file for complete search history.

(56) References Cited

U.S. PATENT DOCUMENTS

| | | | |
|---|---|---|---|
| 2,711,586 A * | 6/1955 | Groves | 433/95 |
| 3,908,637 A | 9/1975 | Doroshow | |
| 3,958,566 A | 5/1976 | Furihata | |
| 4,031,896 A | 6/1977 | Ronnmark | |
| 4,146,019 A | 3/1979 | Bass et al. | |
| 4,198,958 A | 4/1980 | Utsugi | |
| 4,243,040 A | 1/1981 | Beecher | |
| 4,253,448 A | 3/1981 | Terada | |
| 4,270,525 A | 6/1981 | Furihata | |
| 4,408,598 A | 10/1983 | Ueda | |
| 4,412,531 A | 11/1983 | Chikashige | |
| 4,430,073 A | 2/1984 | Bemis et al. | |
| 4,468,216 A | 8/1984 | Muto | |
| 4,469,090 A | 9/1984 | Konomura | |
| 4,469,100 A | 9/1984 | Hardwick | |
| 4,561,428 A | 12/1985 | Konomura | |

(Continued)

FOREIGN PATENT DOCUMENTS

EP 0958787 11/1999

(Continued)

OTHER PUBLICATIONS

White, Frank M., Fluid Mechanics, Copyright 1986, McGraw-Hill, Inc. 2nd Edition, pp. 332-339.*

(Continued)

*Primary Examiner*—Anhtuan T Nguyen
*Assistant Examiner*—Elizabeth Houston

(57) ABSTRACT

A stone retrieval suction device facilitates the retention and then relocation and/or removal of objects disposed in a patient's urinary system. The device includes an elongated member for placement in a channel of a flexible ureteroscope. The elongated member defines a suction passageway which extends longitudinally therethrough. The elongated member is flexible enough to bend with the flexible ureteroscope, and it is strong enough to prevent collapse of the suction passageway when suction is provided through the suction passageway by a vacuum source. The elongated member includes a distal portion for contacting and retaining an object when the suction is provided.

12 Claims, 24 Drawing Sheets

U.S. PATENT DOCUMENTS

| | | | |
|---|---|---|---|
| 4,562,830 A | 1/1986 | Yabe | |
| 4,572,163 A | 2/1986 | Collins et al. | |
| 4,616,631 A | 10/1986 | Takahashi | |
| 4,643,197 A | 2/1987 | Greene et al. | |
| 4,672,953 A | 6/1987 | DiVito | |
| 4,686,965 A | 8/1987 | Bonnet et al. | |
| 4,759,348 A | 7/1988 | Cawood | |
| 4,794,913 A | 1/1989 | Shimonaka et al. | |
| 4,807,626 A | 2/1989 | McGirr | |
| 4,813,926 A | 3/1989 | Kerwin | |
| 4,832,048 A | 5/1989 | Cohen | |
| 4,878,900 A | 11/1989 | Sundt | |
| 4,898,574 A | 2/1990 | Uchiyama et al. | |
| 4,899,733 A | 2/1990 | DeCastro et al. | |
| 4,973,311 A | 11/1990 | Iwakoshi et al. | |
| 4,982,726 A | 1/1991 | Taira | |
| 5,057,080 A | 10/1991 | Takahashi | |
| 5,059,178 A * | 10/1991 | Ya | 604/101.03 |
| 5,127,393 A | 7/1992 | McFarlin et al. | |
| 5,129,910 A | 7/1992 | Phan et al. | |
| 5,190,050 A | 3/1993 | Nitzsche | |
| 5,199,417 A | 4/1993 | Muller et al. | |
| 5,222,949 A | 6/1993 | Kaldany | |
| 5,226,885 A | 7/1993 | Takahashi | |
| 5,244,459 A | 9/1993 | Hill | |
| 5,257,773 A | 11/1993 | Yoshimoto et al. | |
| 5,269,785 A | 12/1993 | Bonutti | |
| 5,295,830 A | 3/1994 | Shen et al. | |
| 5,299,561 A | 4/1994 | Yoshimoto | |
| 5,320,627 A | 6/1994 | Sorensen et al. | |
| 5,322,263 A | 6/1994 | Yoshimoto et al. | |
| 5,334,171 A | 8/1994 | Kaldany | |
| 5,392,764 A | 2/1995 | Swanson et al. | |
| 5,403,317 A | 4/1995 | Bonutti | |
| 5,453,088 A | 9/1995 | Boudewijn et al. | |
| 5,476,450 A | 12/1995 | Ruggio | |
| 5,569,219 A | 10/1996 | Hakki et al. | |
| 5,718,709 A | 2/1998 | Considine et al. | |
| 5,722,980 A | 3/1998 | Schulz et al. | |
| 5,725,478 A | 3/1998 | Saad | |
| 5,730,742 A * | 3/1998 | Wojciechowicz | 606/49 |
| 5,788,681 A | 8/1998 | Weaver et al. | |
| 5,813,856 A | 9/1998 | Lee | |
| 5,843,028 A | 12/1998 | Weaver et al. | |
| 5,879,342 A | 3/1999 | Kelley | |
| 5,891,114 A | 4/1999 | Chien et al. | |
| 5,935,131 A | 8/1999 | Bonutti | |
| 5,938,645 A | 8/1999 | Gordon | |
| 5,947,988 A | 9/1999 | Smith | |
| 5,975,897 A | 11/1999 | Propp et al. | |
| 6,095,971 A | 8/2000 | Takahashi | |
| 6,174,313 B1 | 1/2001 | Bonutti | |
| 6,197,014 B1 | 3/2001 | Samson et al. | |
| 6,280,415 B1 * | 8/2001 | Johnson | 604/118 |
| 7,278,972 B2 | 10/2007 | Lamoureux et al. | |
| 7,309,334 B2 | 12/2007 | von Hoffmann | |

FOREIGN PATENT DOCUMENTS

WO    WO 00/12011    3/2000

OTHER PUBLICATIONS

International Search Report for International Patent Application No. PCT/US03/23078, 9 pages.

* cited by examiner

MEDICAL DEVICE

CROSS-REFERENCE TO RELATED APPLICATIONS

This application is a divisional application of U.S. patent application Ser. No. 10/202,978, filed Jul. 25, 2002, now abandoned entitled "Medical Device," which is incorporated herein by reference in its entirety.

TECHNICAL FIELD

The invention relates generally to medical devices.

BACKGROUND INFORMATION

Typical stone retrieval devices are used for retrieving objects, such as kidney stones, that are disposed in easily-accessed areas of a patient's urinary tract. Some known stone retrieval devices are configured such that a physician must advance the device past the object, deploy a basket, and then pull the device back toward the object to capture the object in the basket. In situations where the object is embedded in tissue or located in a lower calyx of a patient's kidney, the device cannot be advanced beyond the object and therefore cannot capture the object. Stone retrieval devices configured with graspers can be used to try to retrieve stones embedded in tissue or located in the lower calyx. These devices typically are not very flexible, however, and therefore frequently are not useful in reaching and capturing such objects. Further, grasping stone retrieval devices may not be able to retrieve a certain object due to the size and/or shape of that object.

SUMMARY OF THE INVENTION

Objects, such as kidney stones and other natural or foreign materials, can become trapped in a patient's urinary system. These objects can be disposed in areas of the urinary system which are not easily accessed by currently available stone retrieval devices. The present invention relates to medical retrieval devices and related methods for accessing and then retaining, relocating, and/or removing an object disposed in an internal location of a patient's body (such as the urinary system) which is not easily accessed by currently available retrieval devices.

In one aspect, the invention involves a medical device. The medical device includes an elongated member that is configured for placement in a channel of a flexible ureteroscope. The elongated member defines a suction passageway which extends longitudinally therethrough. The elongated member bends with the flexible ureteroscope when placed within the channel of the flexible ureteroscope. The suction passageway resists collapsing when suction is provided through the suction passageway by a vacuum source. The elongated member includes a proximal portion for communicating with the vacuum source to provide the suction through the suction passageway and a distal portion for contacting an object and retaining the object in contact with the distal portion when the suction is provided through the suction passageway.

Embodiments according to this aspect of the invention can include various features. For example, the distal portion can include a tapered tip. The distal portion can include a tip which includes a concave portion for contacting the object and retaining the object in contact with the concave portion when the suction is provided through the suction passageway. The distal portion can include a tip which includes a plurality of members extending radially outward from the tip. The plurality of members prevent tissue proximate to the object from being drawn into the suction passageway when suction is provided through the suction passageway. The distal portion can include a tip which includes a concave portion. The concave portion prevents tissue proximate the object from being drawn into the suction passageway when the suction is provided through the suction passageway. The elongated member can include a mesh to reinforce the member and thus resist collapse of the suction passageway when suction is provided. The mesh can extend longitudinally and circumferentially along the elongated member. The mesh can include stainless steel. The elongated member can include a coil which extends longitudinally. and circumferentially along the elongated member. The proximal portion can include a luer connector and/or a handle for connecting to the vacuum source. The handle can include a switch for selectively enabling and disabling the suction through the suction passageway. The proximal portion can be in communication with a regulator for regulating the suction through the suction passageway. The elongated member can be made of a material such as a biocompatible plastic, a biocompatible polyurethane, or a biocompatible rubber, for example. The elongated member can have an outside diameter of between two and three french. At least some of the distal portion can be radiopaque.

In another aspect, the invention involves a method of contacting and moving an object disposed in a patient. The method includes providing a vacuum source, providing a flexible ureteroscope and introducing the ureteroscope into a patient, and providing a medical device. The medical device includes an elongated member that is configured for placement in a channel of the flexible ureteroscope. The elongated member defines a suction passageway extending longitudinally therethrough. The elongated member bends with the ureteroscope when the elongated member is placed within the channel of the flexible ureteroscope. The suction passageway resists collapsing when suction is provided through the suction passageway by the vacuum source. The elongated member includes a proximal portion for communicating with the vacuum source to provide the suction through the suction passageway, and a distal portion for contacting an object and retaining the object in contact with the distal portion when the suction is provided through the suction passageway. The method further includes introducing the medical device into the channel of the flexible ureteroscope, providing suction through the suction passageway and retaining the object in contact with the distal portion, and moving the retained object from a first location in the patient to a second location.

Embodiments according to this aspect of the invention can include various features. For example, the method can further include moving the retained object to a second location. Moving the retained object to a second location can include moving the retained object outside the patient or to another location inside the patient.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Objects, such as kidney stones (calculi) and other natural or foreign materials, can become trapped in a patient's urinary system. These objects can be disposed in areas of the urinary system that are easily accessed by currently available stone retrieval devices. These objects can also be disposed in areas of the urinary system, such as embedded in tissue or located in a lower calyx of a patient's kidney, for example, which are not easily accessed by currently available stone retrieval devices. The present invention relates to medical devices and related methods for accessing and then retaining, relocating, and/or removing an object disposed in an internal area of a patient's body (such as the urinary system) which is difficult or impossible to access with currently available retrieval devices or methods.

Figure 1A:
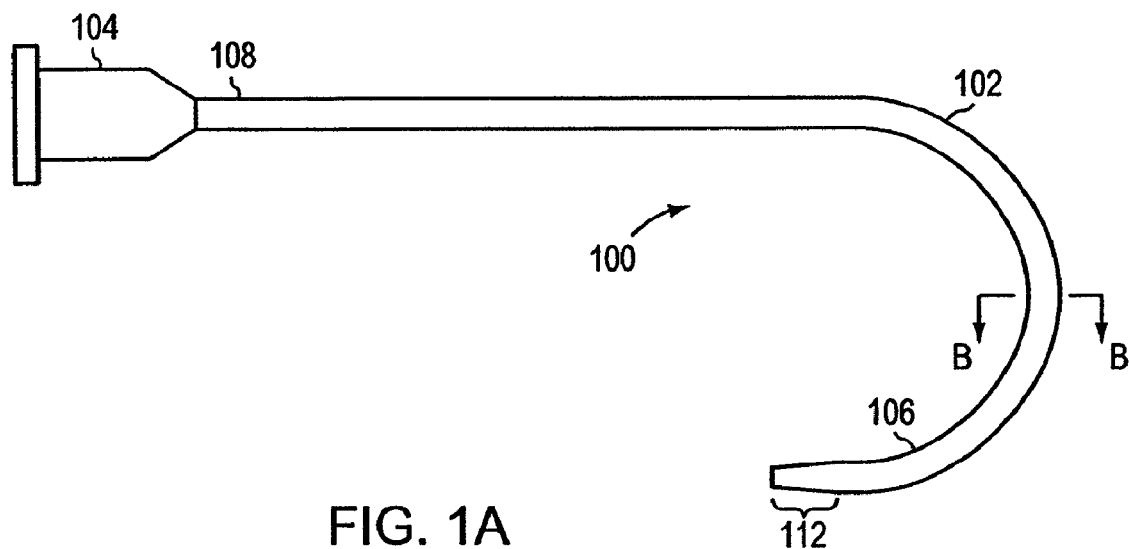
FIG. 1A is an illustrative diagram of a stone retrieval suction device, according to one embodiment of the invention.
Figure 1B:
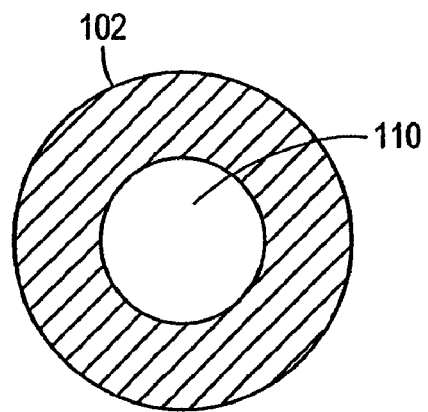
FIG. 1B is an illustrative cross sectional view of the stone retrieval suction device of FIG. 1A, taken along line B-B in FIG. 1A.
Figure 2:
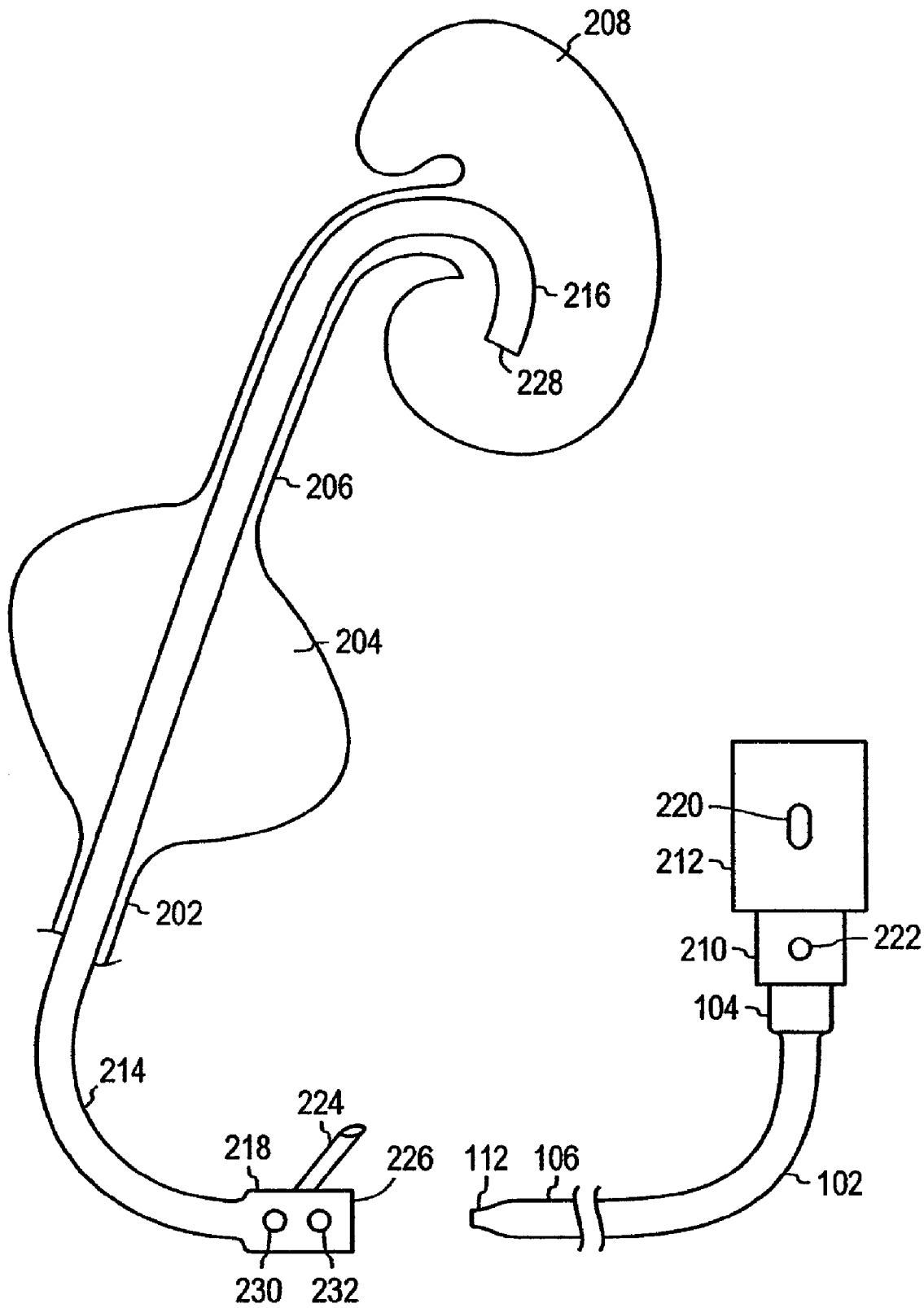
FIG. 2 is an illustrative diagram of a flexible ureteroscope disposed in a patient and a stone retrieval suction device in communication with a vacuum source disposed outside of the patient, according to one embodiment of the invention.
Figure 3:
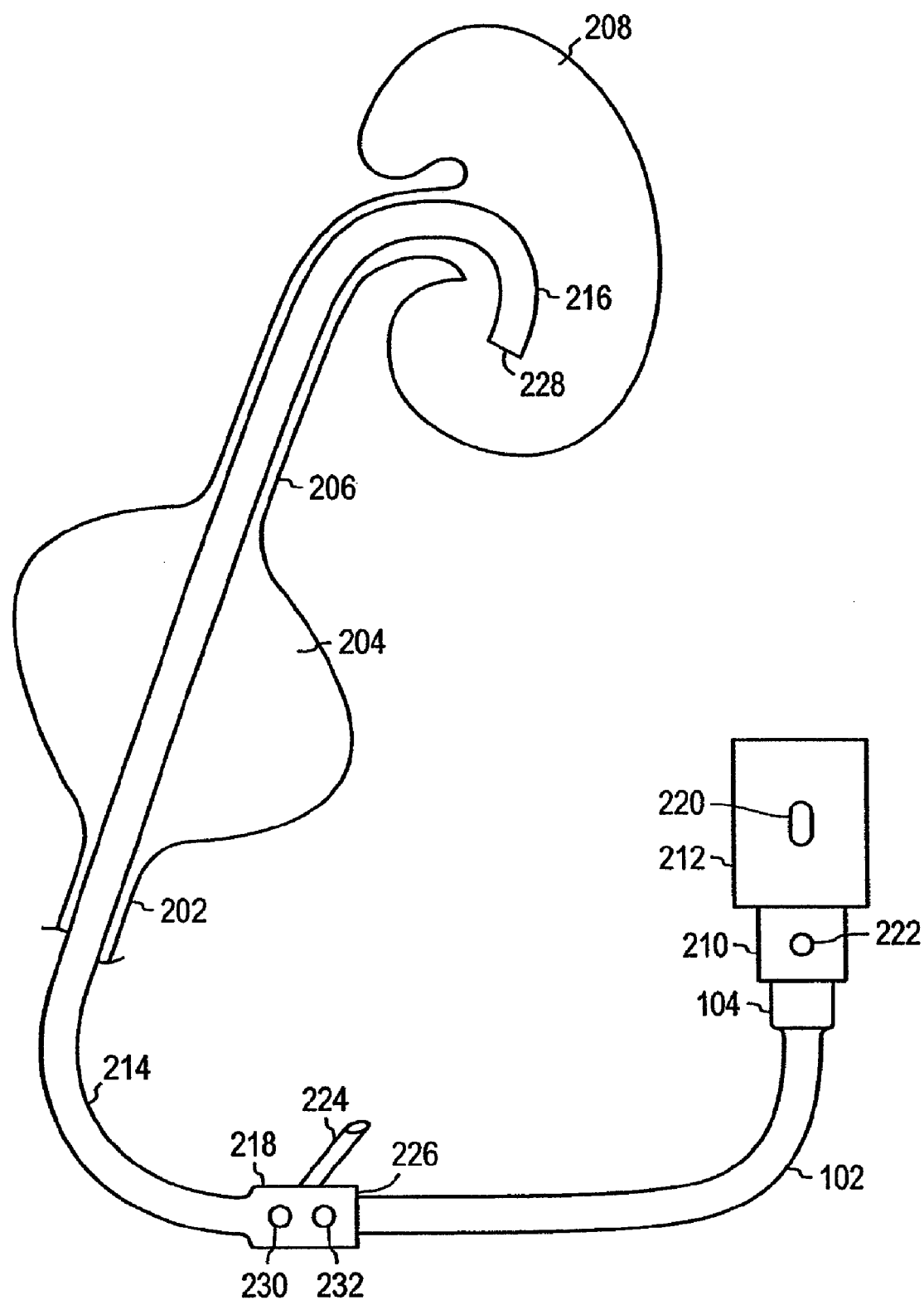
FIG. 3 is an illustrative diagram of the stone retrieval suction device of FIG. 2 partially disposed in a channel of the flexible ureteroscope.

Referring to FIGS. 1A and 1B, in one embodiment, the stone retrieval suction device 100 includes an elongated member 102 which defines a suction passageway 110 extending longitudinally therethrough. The elongated member 102 is designed to be placed in a channel of a flexible ureteroscope and has an outside diameter of between two and three french. The elongated member 102 bends with the flexible ureteroscope when placed within the channel of the flexible ureteroscope. The suction passageway 110 resists collapsing when suction is provided through the suction passageway 110 by a vacuum source. For example, the elongated member 102 can be reinforced to resist collapse of the suction passageway 110 when suction is provided through the suction passageway 110. Materials that can be used for the elongated member 102 include, but are not limited to, biocompatible plastic, biocompatible rubber, and biocompatible polyurethane. In one embodiment, the bendable elongated member 102 is formed of Pebax, PTFE, or Polyuethane. The elongated member further includes a proximal portion 108. The proximal portion 108 is in communication with the vacuum source to provide suction through the suction passageway 110. In one embodiment, the proximal portion 108 can also include a luer connector 104. The luer connector 104 is used to connect the elongated member 102 to the vacuum source. The elongated member further includes a distal portion 106 for making contact with an object disposed in a patient, such as a kidney stone. The distal portion 106 retains the object in contact with the distal portion 106 when suction is provided through the suction passageway 110. In one embodiment, the distal portion 106 can also include a tapered tip 112 which is used to contact the object. In other embodiments, the distal portion 106 can include other types of tips which are discussed in further detail below. In some embodiments, the distal portion 106 can also include a radiopaque material which facilitates easily locating the elongated member 102 with a fluoroscope when the elongated member 102 is disposed within the patient. The radiopaque material can be painted on, and/or embedded in, the elongated member 102. The radiopaque material can also be a band painted on, embedded in, and/or wrapped around the distal portion 106 of the elongated member 102. In some embodiments, the radiopaque material can be tungsten filled ink, bismuth subcarbonate, or barium sulfate. In other embodiments, the radiopaque material can be a platinum or tantalum metal band.

The elongated member 102 can be extruded from any of the materials previously described using known extrusion techniques. The luer connector 104 can be made of molded plastic or metal, such as stainless steel. The tapered tip 112 can also be made of molded plastic or metal.

Referring to FIGS. 2-4A, in operation, a user (e.g. a doctor or other medical personnel) inserts a distal end 216 of a flexible ureteroscope 214 into the patient's urethra 202. The user advances the flexible ureteroscope 214 so that the distal end 216 passes into and through the urinary bladder 204, into and through the ureter 206, and into the kidney 208. The user positions the distal end 216 of the flexible ureteroscope 214 within the patient's kidney 208 by manipulating positioning knobs 230, 232. The knob 230 moves the distal end 216 vertically and the knob 232 moves the distal end 216 horizontally. By manipulating the positioning knobs 230, 232, and viewing the kidney's 208 interior with an eyepiece 224, the user can position a distal channel opening 228 of the flexible ureteroscope 214 proximate an object, such as a kidney stone, that is disposed in the patient's kidney 208.

The user then connects the luer connector 104 to a regulator 210 which, in turn, is connected to a vacuum source 212. The vacuum source 212 provides suction through the suction passageway 110 and the regulator 210 allows the user to vary the suction provided by the vacuum source 212 by adjusting a suction adjustment dial 222. In this embodiment, the vacuum source 212 is located near the patient. In another embodiment, the vacuum source 212 can be located remotely and is discussed in further detail below.

As previously described, the elongated member 102 includes a material that enables the elongated member 102 to bend with the flexible ureteroscope 214. After the user has inserted the flexible ureteroscope 214 into the patient, the user then inserts the distal portion 106 of the elongated member 102 into a proximal channel opening 226 at a proximal end 218 of the flexible ureteroscope 214. The user then advances the distal portion 106 through the channel 502 (shown in FIG. 5) of the flexible ureteroscope 214 until the tapered tip 112 extends out of the distal channel opening 228 at the distal end 216 of the flexible ureteroscope 214.

Figure 4A:
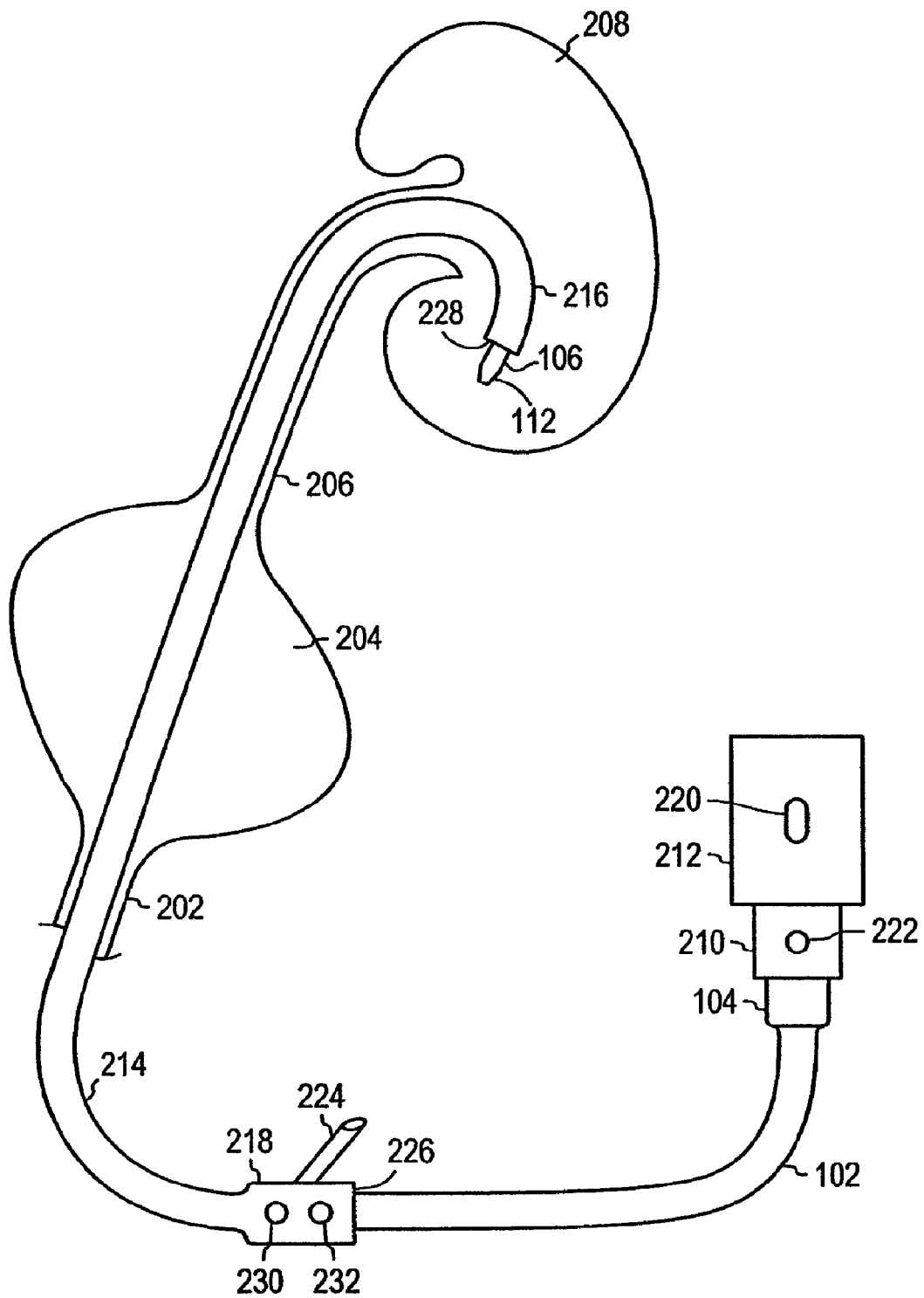
FIG. 4A is an illustrative diagram of the stone retrieval suction device of FIG. 2 disposed in the channel of the flexible ureteroscope and extending out of a distal end of the ureteroscope and into the patient's kidney.
Figure 4B:
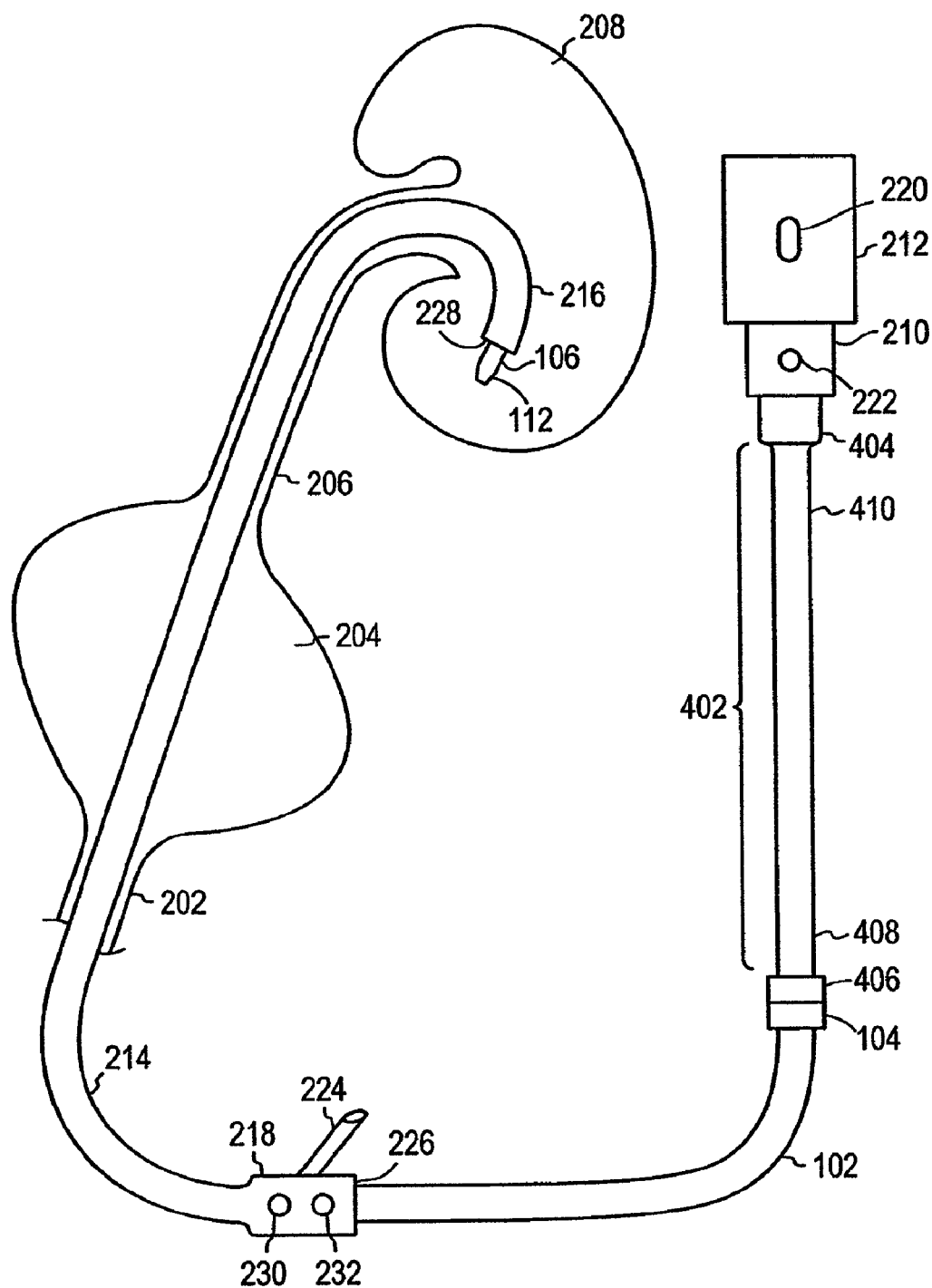
FIG. 4B is an illustrative diagram of a stone retrieval suction device disposed in the channel of the flexible ureteroscope and also in communication with a remote vacuum source through an extension tube, according to another embodiment of the invention.

Referring to FIG. 4B, in another embodiment, the elongated member 102 can be connected to a remotely located vacuum source 212 (such as a vacuum source located on a wall). In this embodiment, the elongated member 102 communicates with the regulator 210 through an extension tube 402. The luer connector 104 of the elongated member 102 is mated to a first luer connector 406 disposed on a proximal end 408 of the extension tube 402. A second luer connector 404 disposed on a distal end 410 of the extension tube is connected to the regulator 210.

Figure 5:
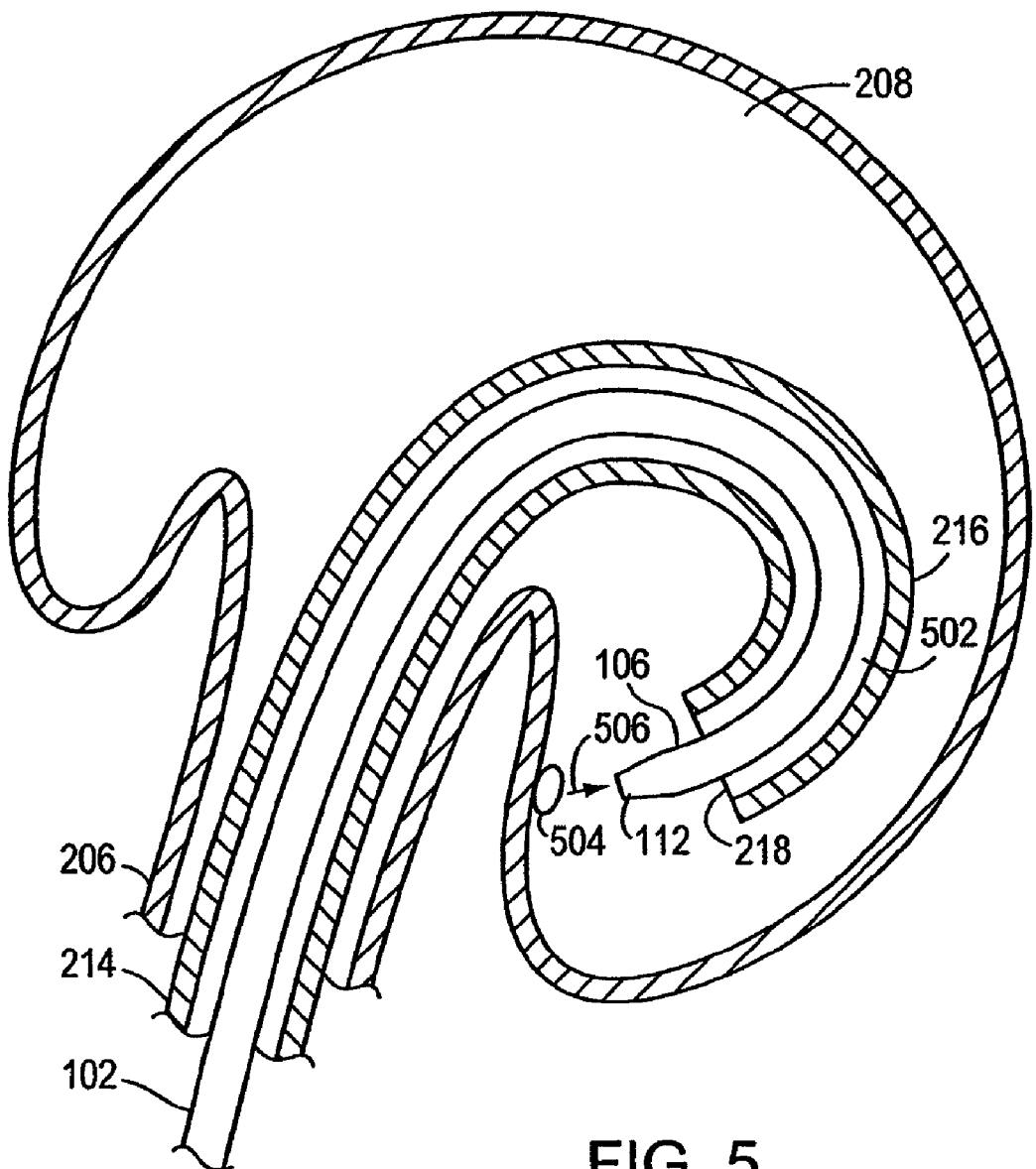
FIG. 5 is an illustrative cross sectional view of a distal portion of a stone retrieval suction device disposed inside the patient and proximate an object disposed in the patient's kidney, according to one embodiment of the invention.
Figure 6:
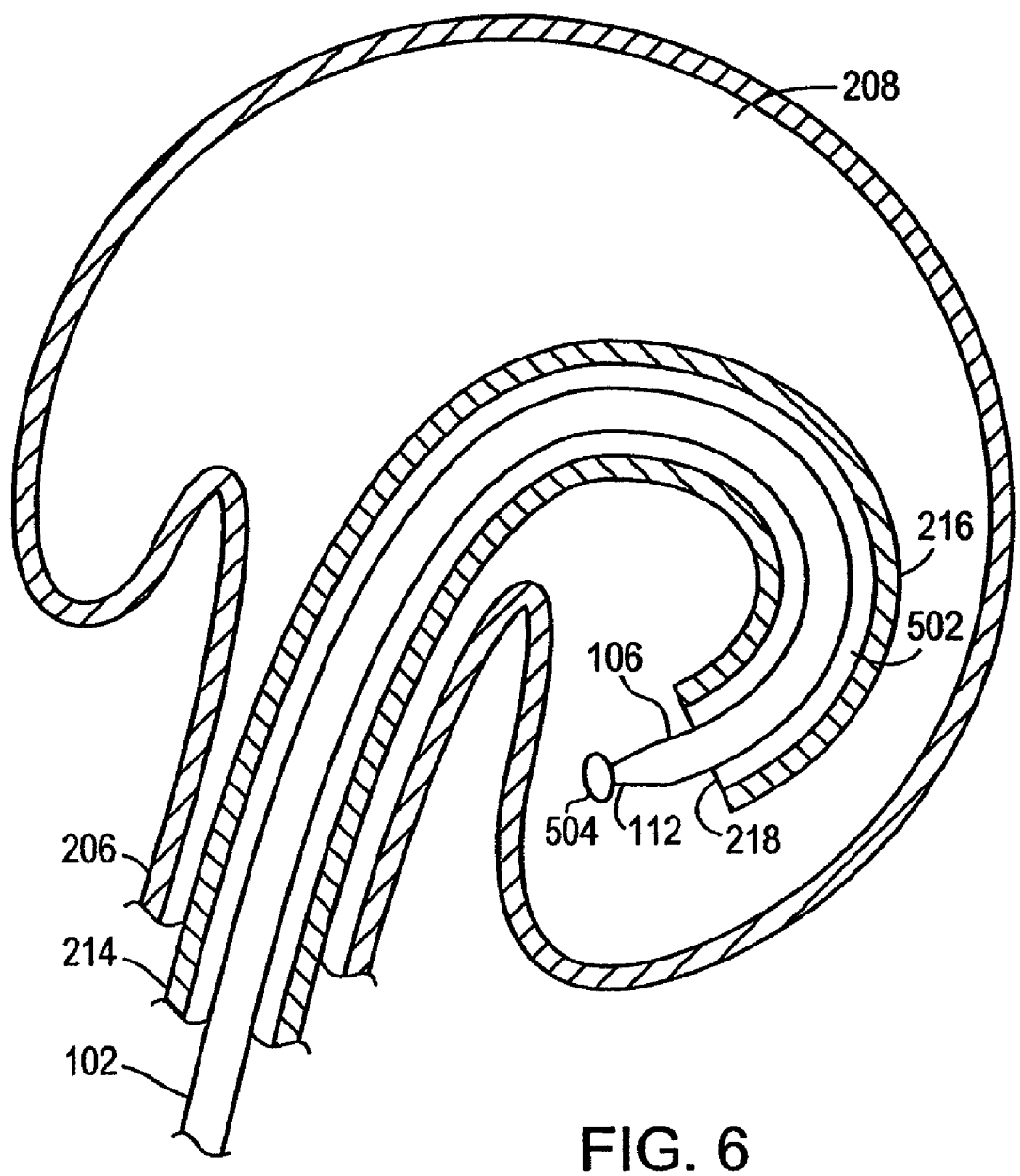
FIG. 6 is an illustrative cross sectional view of the distal portion of the stone retrieval suction device of FIG. 5 contacting and retaining the object disposed in the patient's kidney.

Referring to FIGS. 4A, 5, and 6, after the elongated member 102 is advanced through the channel 502 so that the tapered tip 112 extends out of the channel 502 through the distal channel opening 218 and is proximate to a kidney stone 504, the user switches on the suction (using switch 220). The suction pulls the kidney stone 504 in a direction (indicated by arrow 506) toward the tapered tip 112. Eventually, the kidney stone 504 makes contact with the tapered tip 112 and is held in contact with the tapered tip 112 by the continuous suction through the suction passageway 110 (shown in FIG. 1B). If the kidney stone 504 is embedded in tissue, the user moves the tapered tip 112 toward the embedded kidney stone 504. After the tapered tip 112 makes contact with the embedded kidney stone 504, the suction through the suction passageway 110 retains the kidney stone 504 in contact with the tapered tip 112. The user can then pull the kidney stone 504 free by retracting the distal portion 106 of the elongated member 102 into the channel 502.

This device and method enables the user to capture and retain the kidney stone 504 even when the kidney stone 504 is embedded in tissue or located in a portion of the patient's body that is difficult or impossible to access with typical basket and/or grabber stone retrieval devices.

Figure 7:
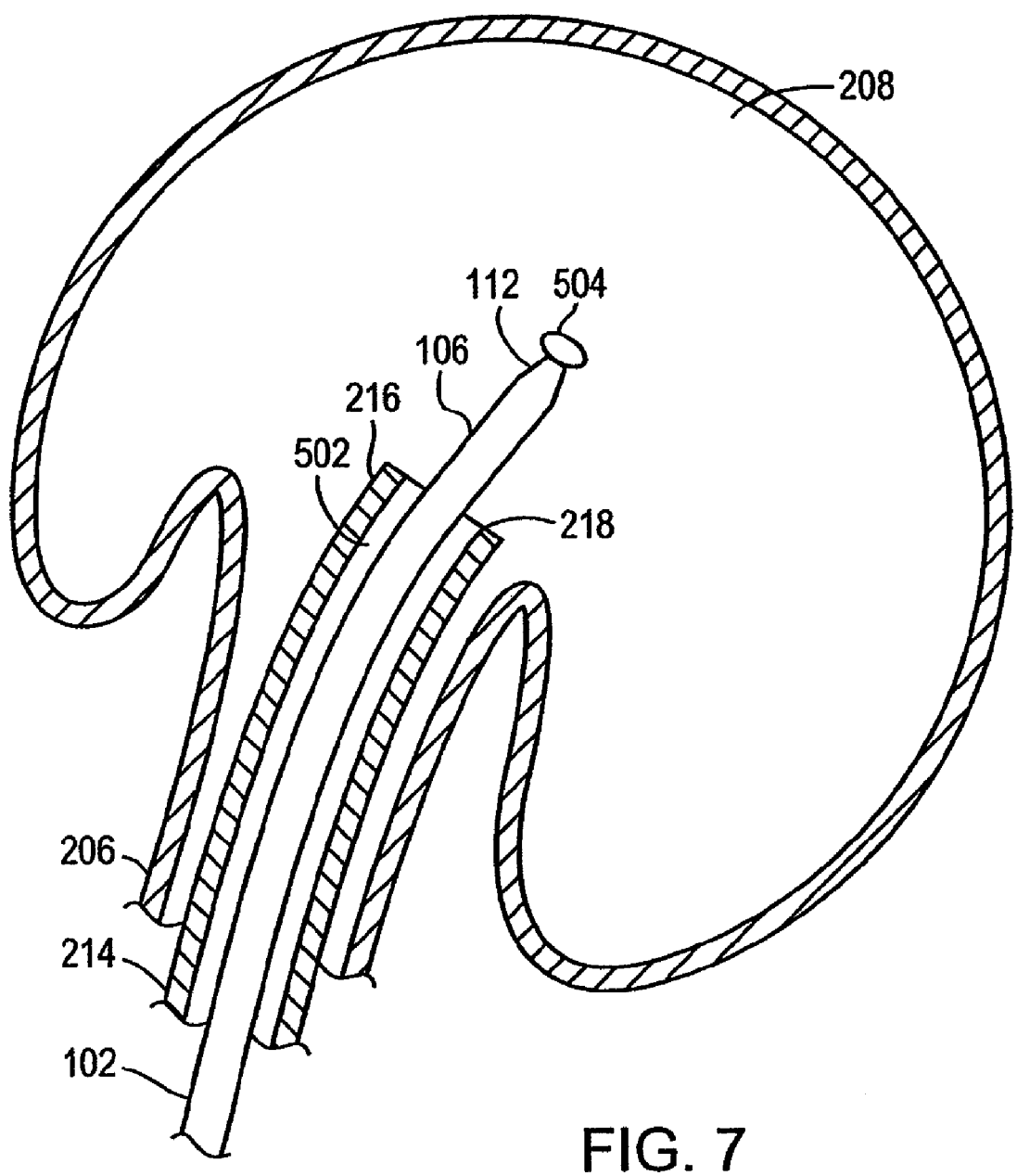
FIG. 7 is an illustrative cross sectional view of the distal portion of the stone retrieval suction device of FIG. 6 after the object disposed in a patient's kidney has been relocated.
Figure 8:
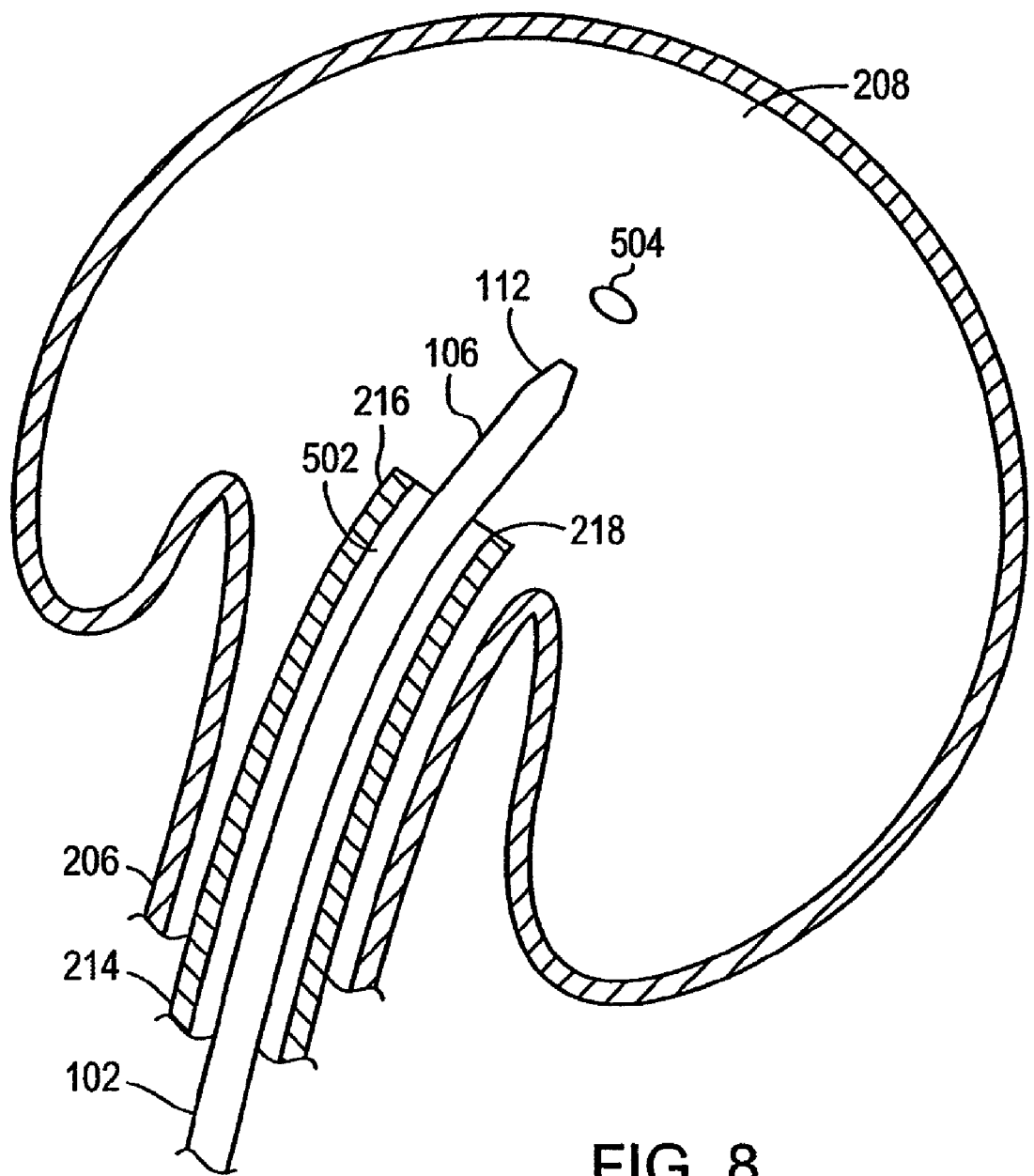
FIG. 8 is an illustrative cross sectional view of the distal portion of the stone retrieval suction device of FIG. 7 after the object disposed in a patient's kidney has been released.
Figure 9:
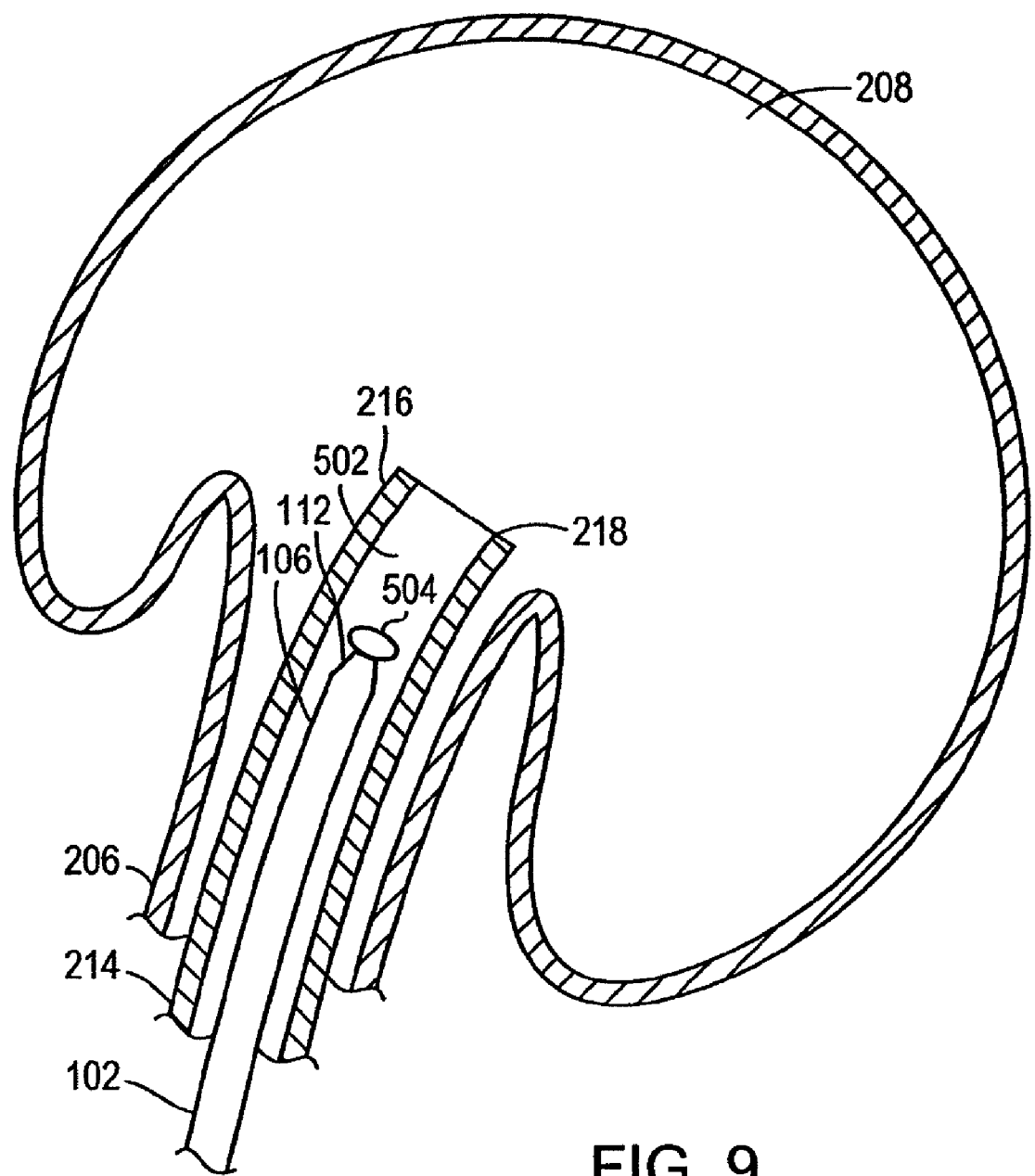
FIG. 9 is an illustrative cross sectional view of the distal portion of the stone retrieval suction device of FIG. 7 removing the object from the patient's kidney.

Referring to FIGS. 7-8, after contacting and retaining the kidney stone 504, the user can reposition the distal end 216 of the flexible ureteroscope 214 with the distal portion 106 of the elongated member 102 still extending beyond the distal channel opening 218 and retaining the kidney stone 504 in contact with the tapered tip 112. The purpose of repositioning the distal end 216 of the flexible ureteroscope 214 is to move the kidney stone 504 to an area in the kidney that is easily accessed by typical stone retrieval baskets or grabbers. After the user relocates the kidney stone 504, the user can release the kidney stone 504 by discontinuing the suction and retracting the distal portion 106 of the elongated member 102 through the distal channel opening 218. After the kidney stone 504 is released, the user can use any of a variety of existing stone retrieval devices to capture and remove the kidney stone 504 from the patient's urinary system. If the kidney stone 504 is too large to remove, the user can employ any of a variety stone destruction devices (such as laser or vibration devices, for example) to break the kidney stone 504 into smaller pieces. If the kidney stone 504 has a diameter smaller than the diameter of the channel 502 of the flexible ureteroscope 214, the user can remove the kidney stone 504 from the patient by pulling the kidney stone 504 through the channel 502 of the flexible ureteroscope 214.

Figure 10A:
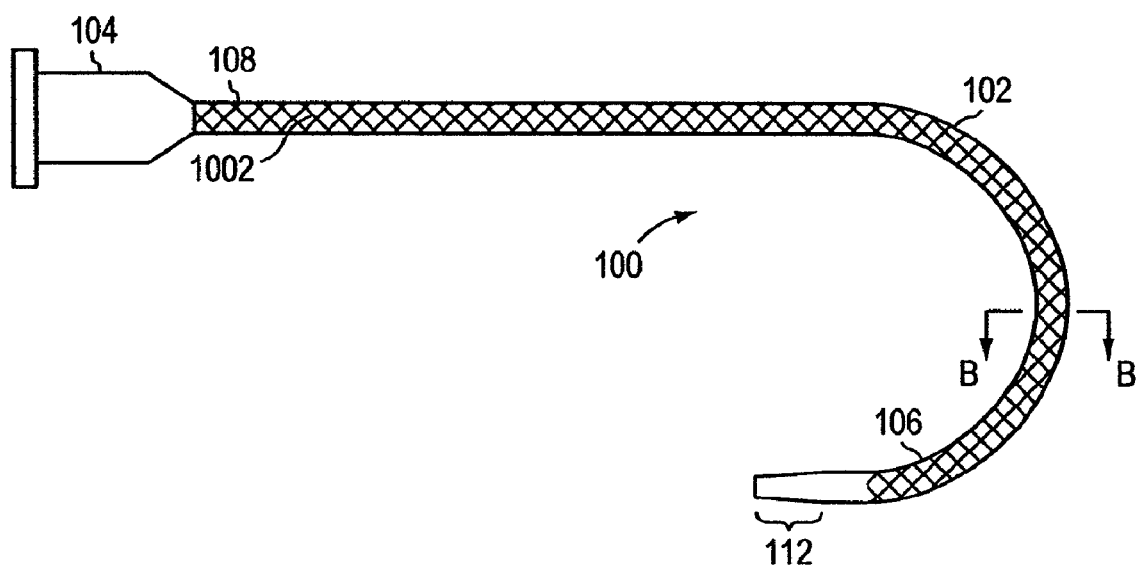
FIG. 10 is an illustrative diagram of a stone retrieval suction device including a mesh, according to another embodiment of the invention.
FIG. 10B is an illustrative cross sectional view of the stone retrieval suction device of FIG. 10A, taken along line B-B in FIG. 10A, according to one embodiment of the invention.
FIG. 10C is an illustrative cross sectional view of the stone retrieval suction device of FIG. 10A, taken along line B-B in FIG. 10A, according to another embodiment of the invention.
FIG. 10D is an illustrative cross sectional view of the stone retrieval suction device of FIG. 10A, taken along line B-B in FIG. 10A, according to still another embodiment of the invention.
Figure 10B:
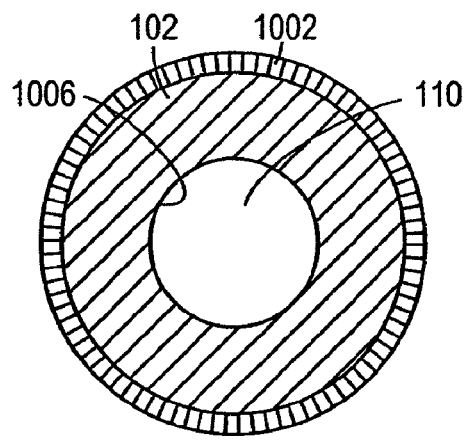
Figure 10C:
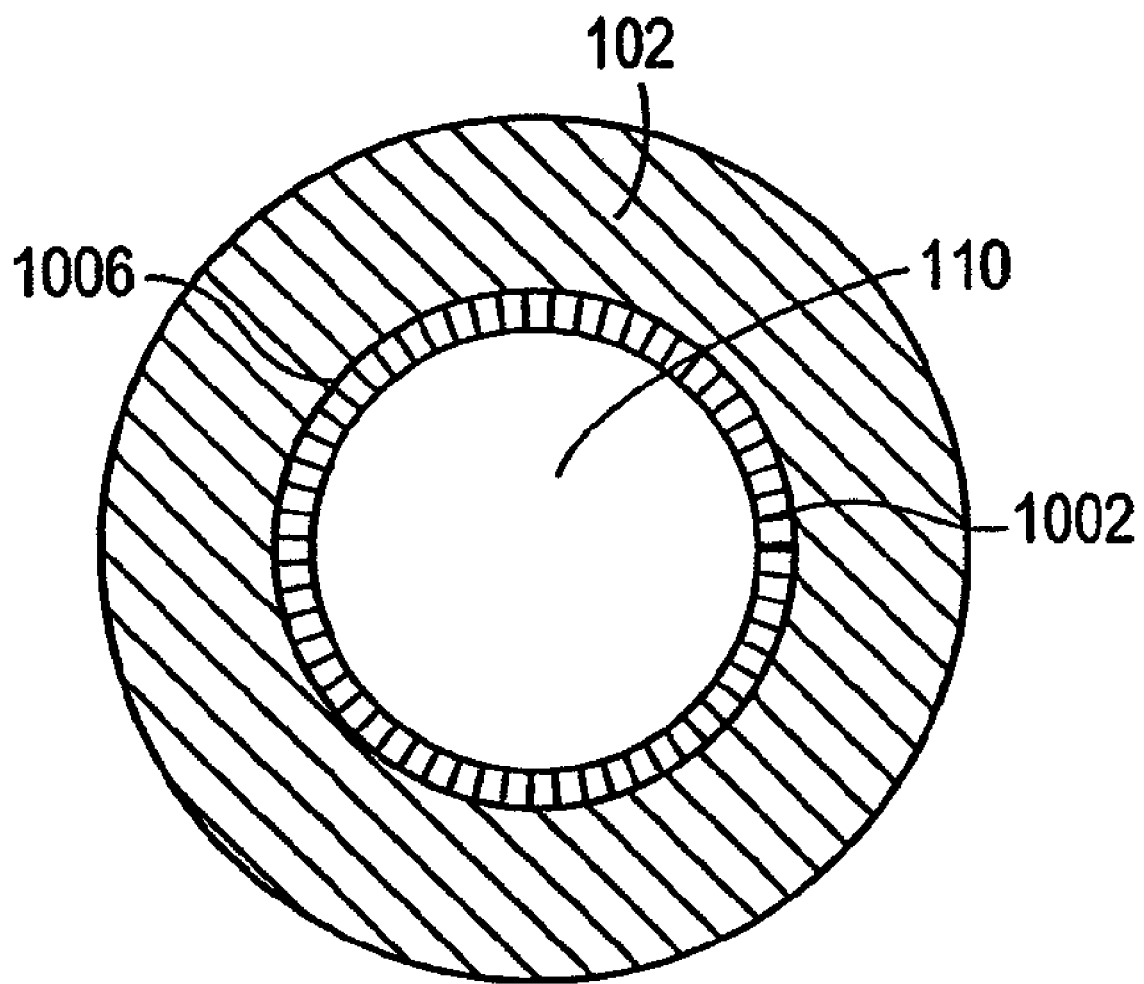
Figure 10D:
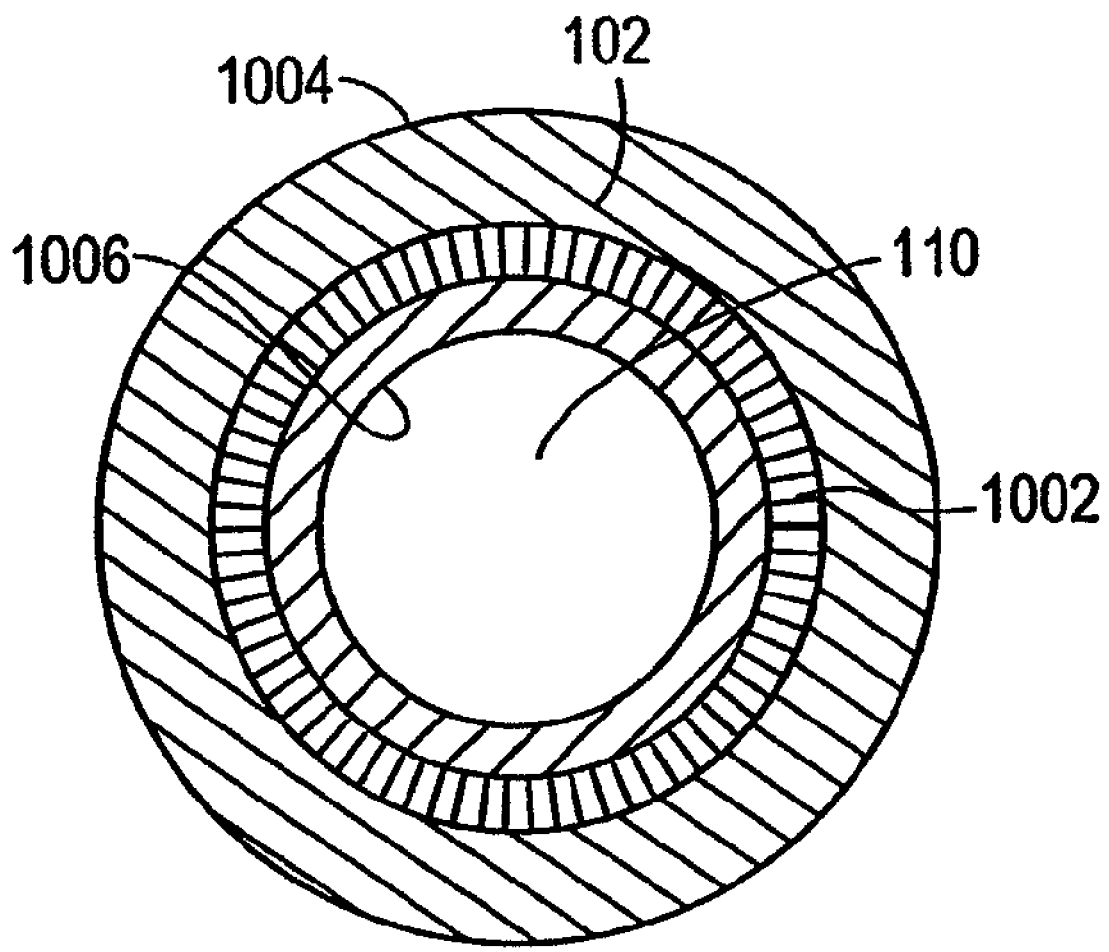
Figure 16:
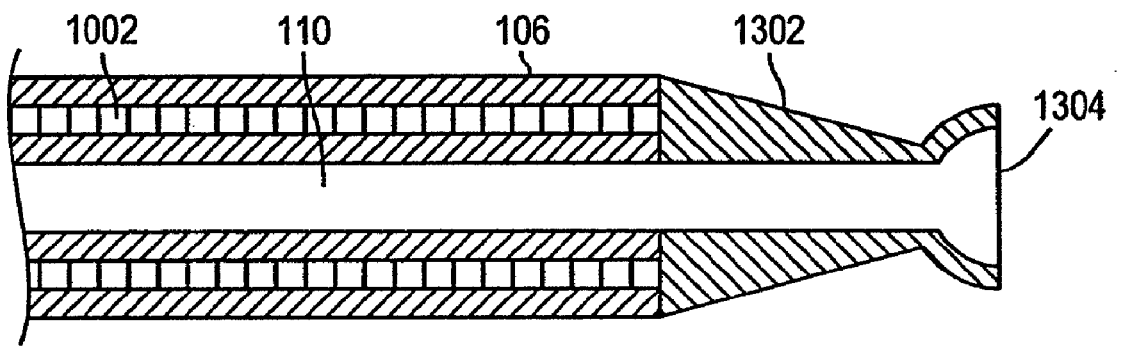
FIG. 16 is an illustrative cross sectional view of a tip including a concave portion coupled to a distal portion of the stone retrieval suction device including a mesh disposed in a wall of the elongated member, according to another embodiment to the invention.
Figure 17:
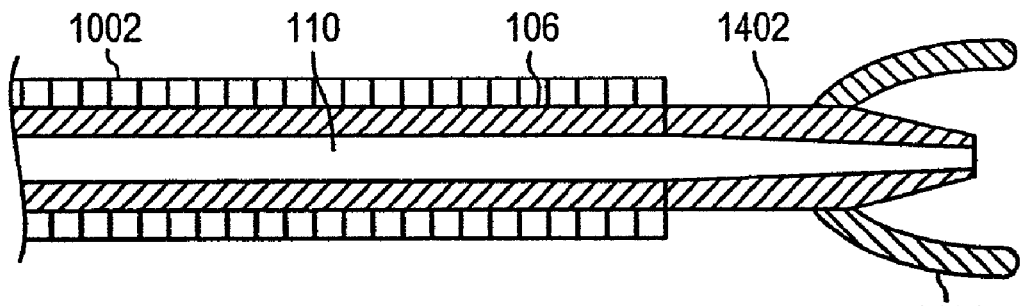
FIG. 17 is an illustrative cross sectional view of a tip including a plurality of arms extending radially outward coupled to a distal portion of the stone retrieval suction device including a mesh disposed on the outer surface of a wall of the elongated member, according to still another embodiment to the invention.
Figure 18:
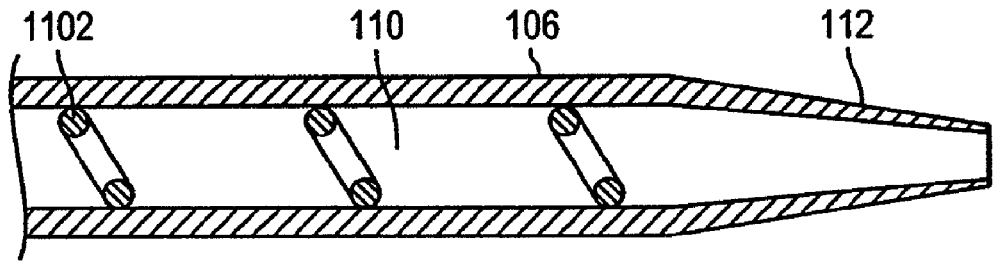
FIG. 18 is an illustrative cross sectional view of a tapered tip coupled to a distal portion of the stone retrieval suction device including a coil disposed on the inner surface of a wall of the elongated member, according to one embodiment to the invention.

Referring to FIGS. 10A-D and 15-17, in another embodiment, the stone retrieval suction device 100 includes a mesh 1002 which extends longitudinally and circumferentially along the elongated member 102. The mesh 1002 can be made of stainless steel and/or other material(s). The mesh 1002 can be, for example, formed by two or more cords that are woven together to form the mesh 1002 with each cord having one or more, for example three or more, component strands. Each of the strands could be thin wire or metal or a metal alloy, for example. The mesh 1002 reinforces the elongated member 102 so that the elongated member 102 does not collapse when suction is provided through the suction passageway 110 by the vacuum source 212 (FIG. 4A). The cords of the mesh 1002 can be either spaced closely together to form a dense mesh or spaced far apart to form a sparse or open mesh. The mesh 1002 can be affixed to an inner surface 1006 (FIGS. 10C and 15) or an outer surface 1004 (FIGS. 10B and 17) of the elongated member 102. The mesh 1002 can also be embedded between the inner surface 1006 and the outer surface 1004 of the elongated member 102 (FIGS. 10D and 16).

Figure 11A:
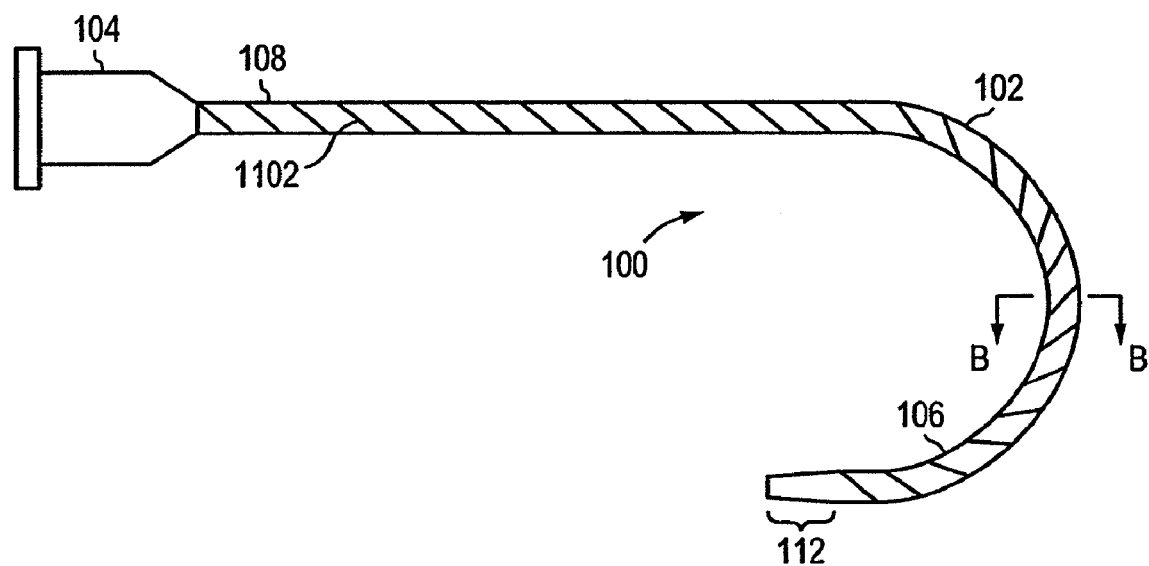
FIG. 11A is an illustrative diagram of a stone retrieval suction device including a coil, according to one embodiment of the invention.
Figure 11B:
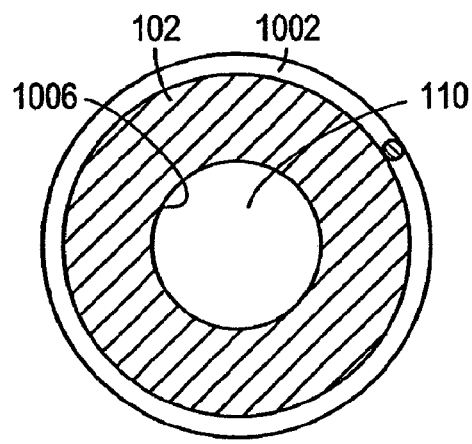
FIG. 11B is an illustrative cross sectional view of the stone retrieval suction device of FIG. 11A, taken along line B-B in FIG. 11A, according to one embodiment of the invention.
Figure 11C:
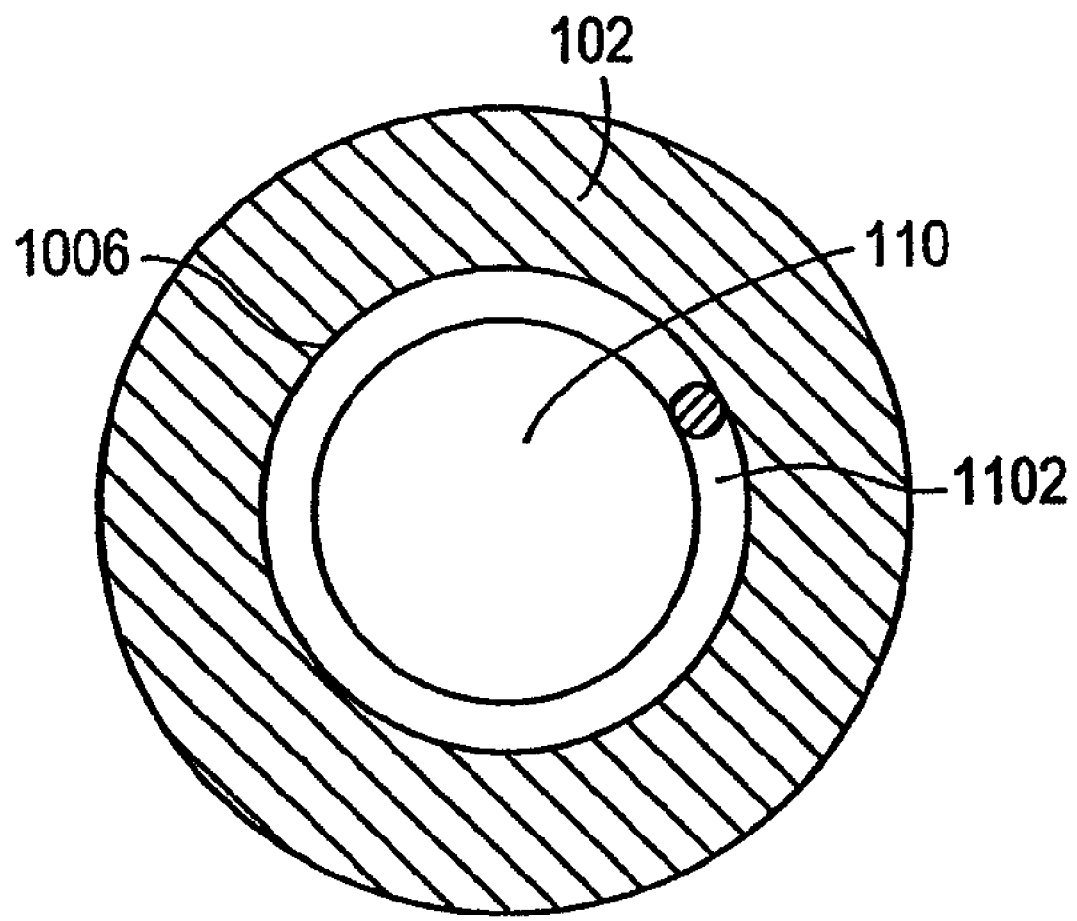
FIG. 11C is an illustrative cross sectional view of the stone retrieval suction device of FIG. 11A, taken along line B-B in FIG. 11A, according to another embodiment of the invention.
Figure 11D:
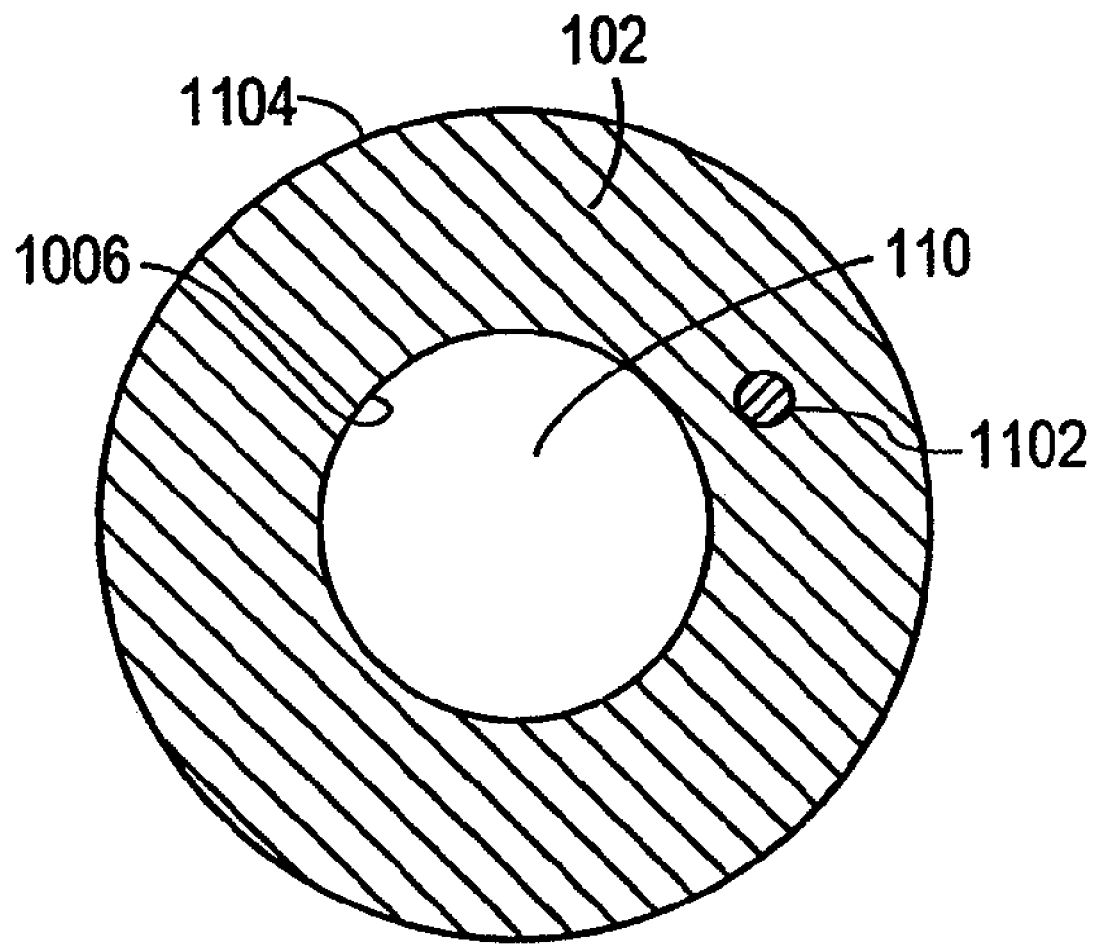
FIG. 11D is an illustrative cross sectional view of the stone retrieval suction device of FIG. 11A, taken along line B-B in FIG. 11A, according to still another embodiment of the invention.
Figure 19:
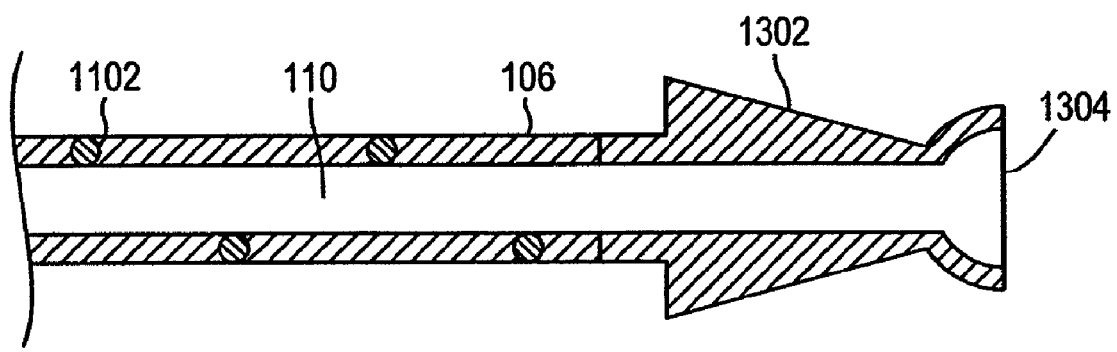
FIG. 19 is an illustrative cross sectional view of a tip including a concave portion coupled to a distal portion of the stone retrieval suction device including a coil disposed in a wall of the elongated member, according to another embodiment to the invention.
Figure 20:
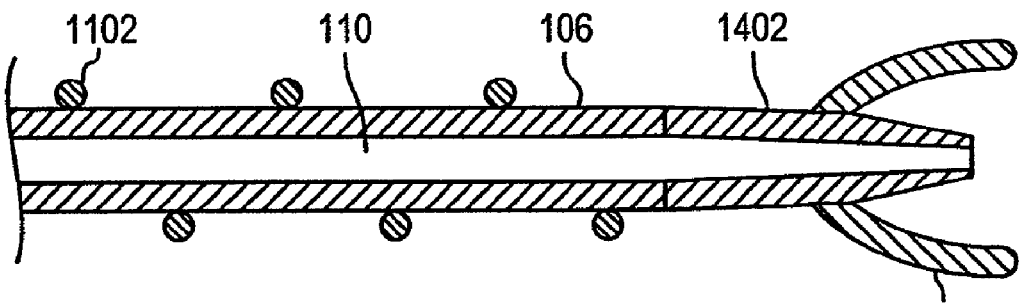
FIG. 20 is an illustrative cross sectional view of a tip including a plurality of arms extending radially outward coupled to a distal portion of the stone retrieval suction device including a coil disposed on the outer surface of a wall of the elongated member, according to still another embodiment to the invention.

Referring to FIGS. 11A-D and 18-20, in still another embodiment, the stone retrieval suction device 100 includes a coil 1102 which extends circumferentially and longitudinally along the elongated member 102. The coil 1102 can be made of stainless steel and/or other material(s). The coil 1102 can be, for example, formed by a cord with the cord having one or more, for example three or more, component strands. Each of the strands could be thin wire or metal or a metal alloy, for example. The coil 1102 reinforces the elongated member 102 so that the elongated member 102 does not collapse when suction is provided through the suction passageway 110 by a vacuum source. The coil 1102 can be tightly wound so that the individual coils are spaced closely together to form a dense coil or the coil 1102 an be loosely wound so that the individual coils are spaced far apart to form an open coil. As with the mesh 1002, the coil 1102 can be affixed to the inner surface 1006 (FIGS. 11C and 18) or the outer surface 1004 (FIGS. 11B and 20) of the elongated member 102. The coil 1102 can also be embedded between the inner surface 1006 and the outer surface 1004 of the elongated member 102 (FIGS. 11D and 19).

Figure 12:
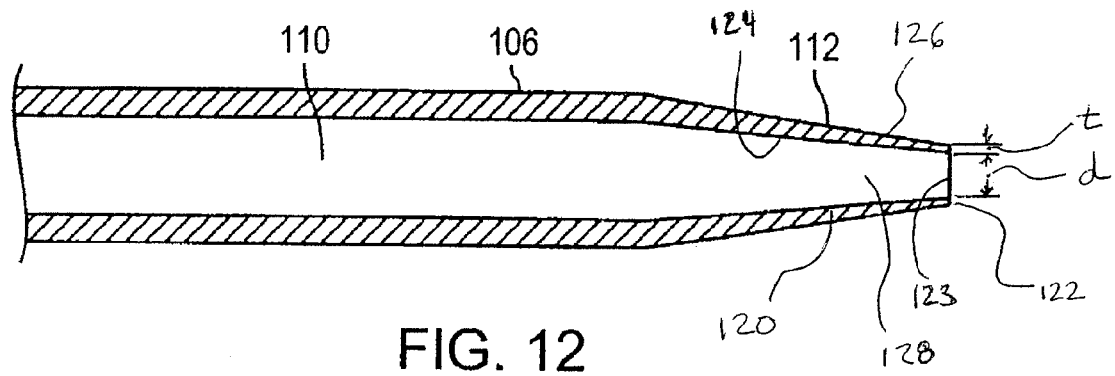
FIG. 12 is an illustrative cross sectional view of a tapered tip coupled to a distal portion of the stone retrieval suction device, according to one embodiment to the invention.
Figure 13A:
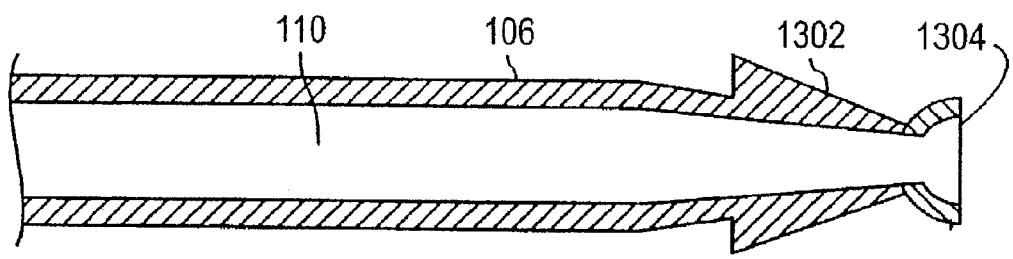
FIG. 13A is an illustrative cross sectional view of a tip including a concave portion coupled to a distal portion of the stone retrieval suction device, according to another embodiment to the invention.
Figure 13B:
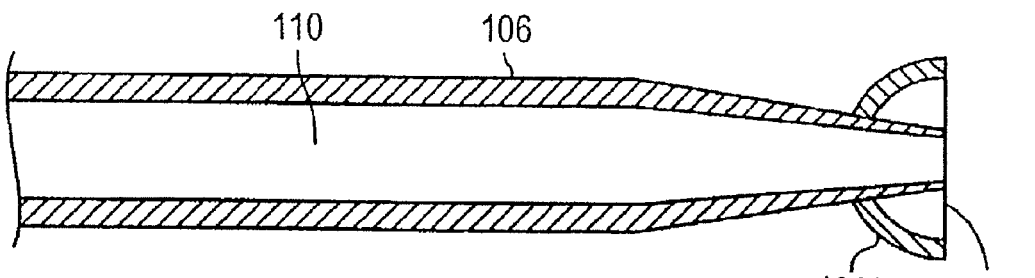
FIG. 13B is an illustrative cross sectional view of a tip including a concave portion coupled to a distal portion of the stone retrieval suction device, according to yet another embodiment to the invention.
Figure 14:
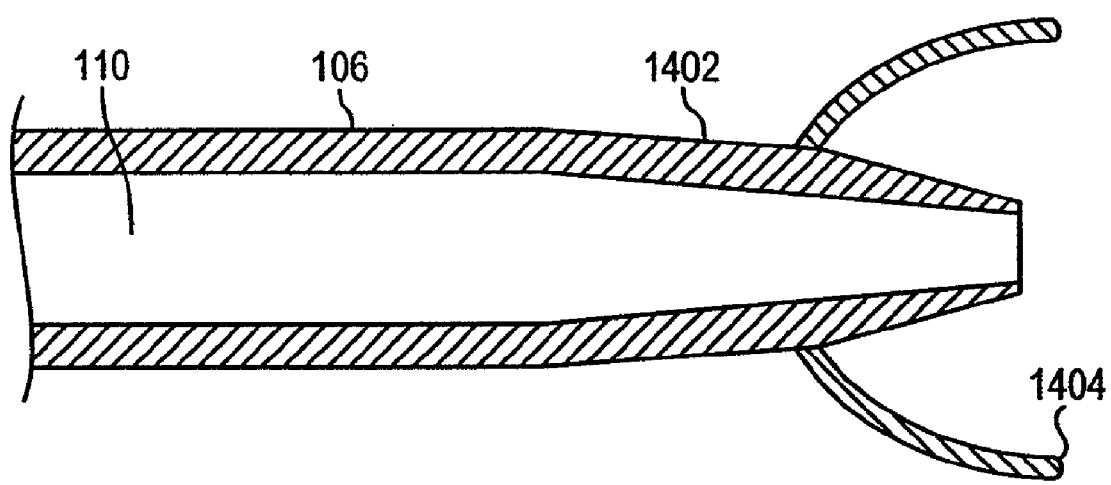
FIG. 14 is an illustrative cross sectional view of a tip including a plurality of arms extending radially outward coupled to a distal portion of the stone retrieval suction device, according to still another embodiment to the invention.
Figure 15:
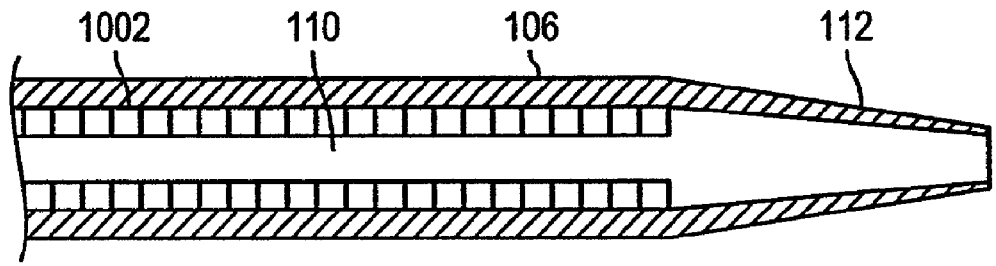
FIG. 15 is an illustrative cross sectional view of a tapered tip coupled to a distal portion of the stone retrieval suction device including a mesh disposed on the inner surface of a wall of the elongated member, according to one embodiment to the invention.

Referring to FIG. 12, the distal portion 106 of the elongated member 102 can include a tapered tip 112. The tapered tip 112 includes a side wall 120 having an inner surface 124, an outer surface 126, and a distal end surface 122. The inner surface 124 of the tapered tip 112 defines a lumen 128 that is a portion of the suction passageway 110. The distal end surface 122 defines a distal end opening 123 in fluid communication with the suction passageway 110. As shown in FIG. 12, the diameter d of the distal end opening 123 is greater than the thickness t of the side wall 120. The tapered tip 112 can be made of molded plastic or metal, for example, although other materials or combinations of materials are possible. In another embodiment shown in FIG. 13A, the distal portion 106 can include a tip 1302 with a concave portion 1304. The concave portion 1304 is used to contact an object disposed in a patient's urinary system and retain the object in contact with the concave portion 1304 when suction is provided through the suction passageway 110. In still another embodiment shown in FIG. 13B, the distal portion 106 can include a concave portion 1306 with a tapered tip 1308 within the concave portion 1306. The concave portion 1306 is used to keep surrounding tissue away from the suction in the tapered tip 1308 when the tapered tip 1308 contacts an object. In yet another embodiment shown in FIG. 14, the distal portion 106 can include a tip 1402 which includes a plurality of members 1404. The plurality of members 1404 extend radially outward from the tip 1402 and prevent tissue (proximate to an object being contacted) from being pulled into the suction passageway 110. The tips 1302, 1402 can also be made of molded plastic or metal.

Figure 21:
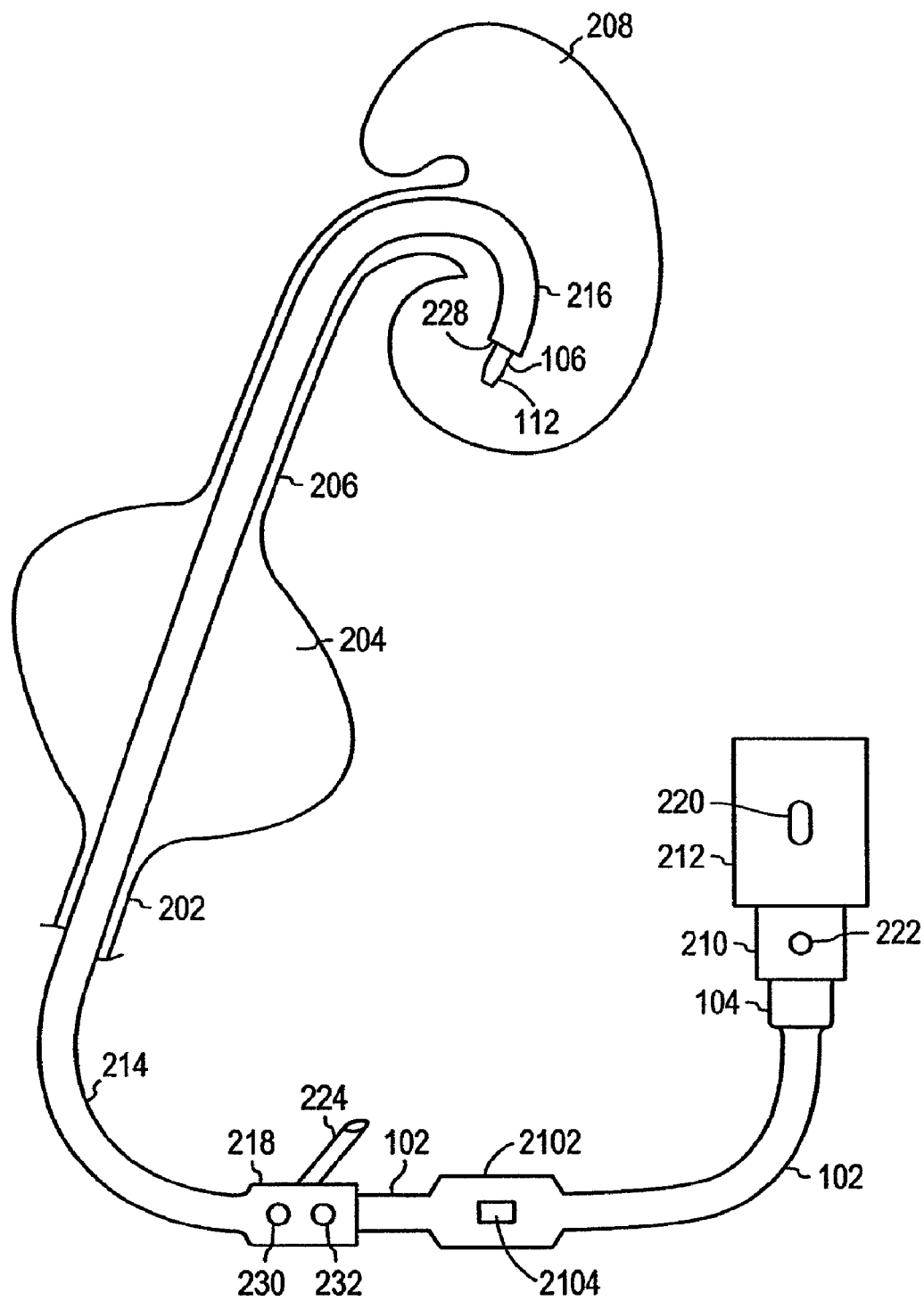
FIG. 21 is an illustrative diagram of the stone retrieval suction device including a handle disposed in the channel of the flexible ureteroscope and extending out of a distal end of the ureteroscope and into the patient's kidney.
Figure 22A:
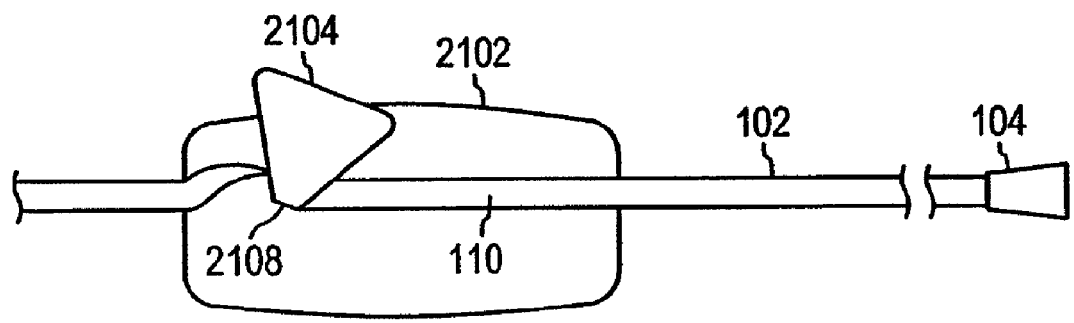
FIGS. 22A and 22B are illustrative cross sectional diagrams of a handle of the stone retrieval suction device, according to one embodiment of the invention.
Figure 22B:
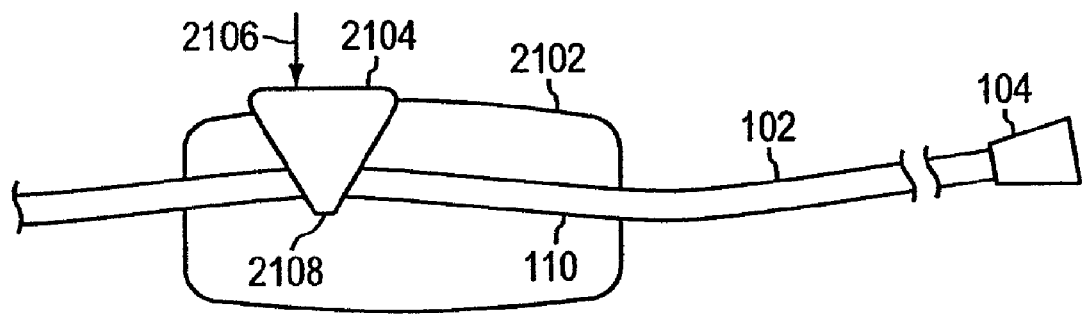

Referring to FIGS. 21, 22A, and 22B, in another embodiment, the suction retrieval device 100 can include a handle 2102. The handle 2102 includes a suction button 2104 which is used to enable and disable the suction in the suction passageway 110 by uncrimping and crimping a portion of the elongated member 102 disposed in the handle 2102. When the suction button 2104 is not pressed (default position), the suction button 2104 is positioned such that a rigid member 2108 presses against the suction tube 302 thereby crimping the elongated member 102 and disabling the suction in the suction passageway 110.

When the suction button 2104 is pressed (in the direction indicated by arrow 2106), the suction button 2104 is positioned such that the rigid member 2108 no longer crimps the elongated member 102, thereby enabling suction in the suction passageway 110. As long as the suction button 2104 is pressed, the suction in the suction passageway 110 is enabled. As soon as the suction button 2104 is released, the suction in the suction passageway 110 is disabled.

In operation, after inserting the flexible ureteroscope 214 into the patient's urinary system, the user connects the luer connector 104 to the regulator 210 and then guides the elongated member 102 into and through the channel of the flexible ureteroscope 214. The user then turns on the vacuum source 212 with the switch 220 and adjusts the suction with suction adjustment knob 222 on the regulator 210. The user positions the elongated member 102 proximate to an object disposed in the patient's urinary system by the method previously described, and then presses the suction button 2104 on the handle 2102 to engage the suction (by uncrimping the portion of elongated member 102 disposed in the handle 2102). After the object is captured and relocated to a new position or removed from the patient, the user releases the button 2104 to disengage the suction (by crimping the portion of elongated member 102 disposed in the handle 2102) thereby releasing the object.

Figure 23A:
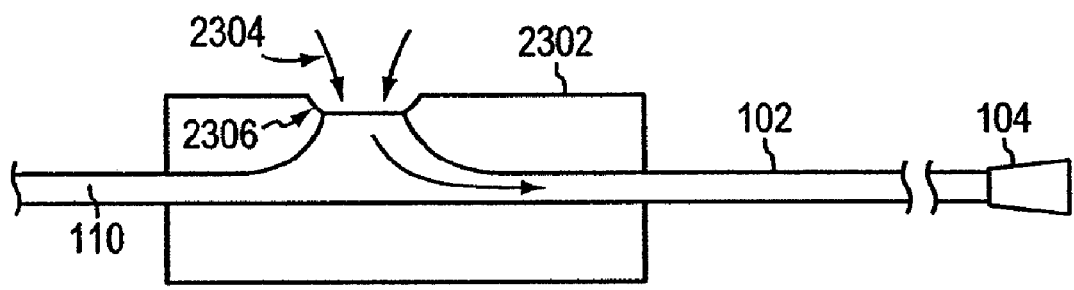
FIGS. 23A and 23B are illustrative cross sectional diagrams of a handle of the stone retrieval suction device, according to another embodiment of the invention.
Figure 23B:
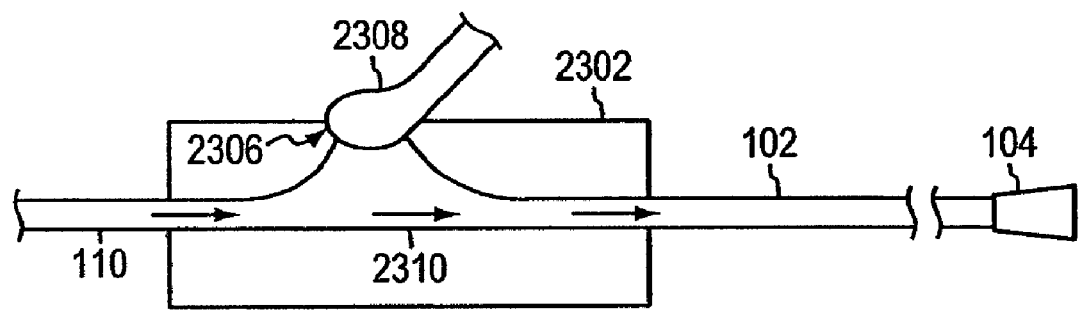

Referring to FIGS. 23A and 23B, in still another embodiment, the suction retrieval device 100 can include a handle 2302. The handle 2302 includes a suction port 2306 which is used to enable and disable the suction in the distal portion 106 of the suction passageway 110. The suction port 2306 is an opening to the suction passageway 110 and allows outside air to be sucked into the suction passageway 110 by the vacuum source (as indicated by arrows 2304) when left open or uncovered. As a result, the suction in the distal portion 106 of the suction passageway 110 is significantly reduced or disabled entirely. When the suction port 2306 is covered, by a user's finger 2308 for example, the suction port 2306 is sealed and the suction in the distal portion 106 of the suction passageway 110 is restored.

Figure 24A:
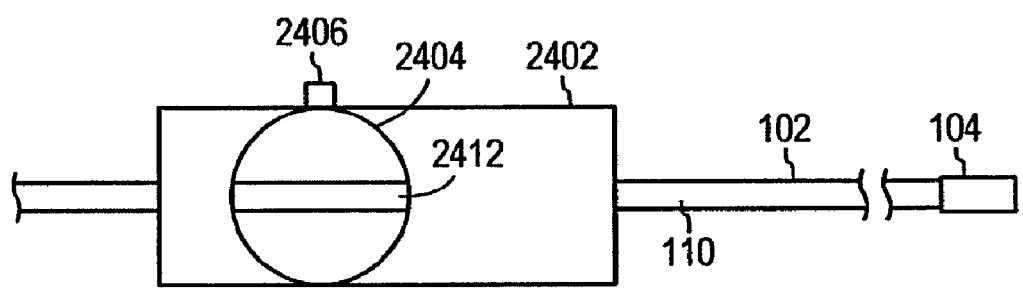
FIG. 24A is an illustrative diagram of a handle of the stone retrieval suction device, according to still another embodiment of the invention.
Figure 24B:
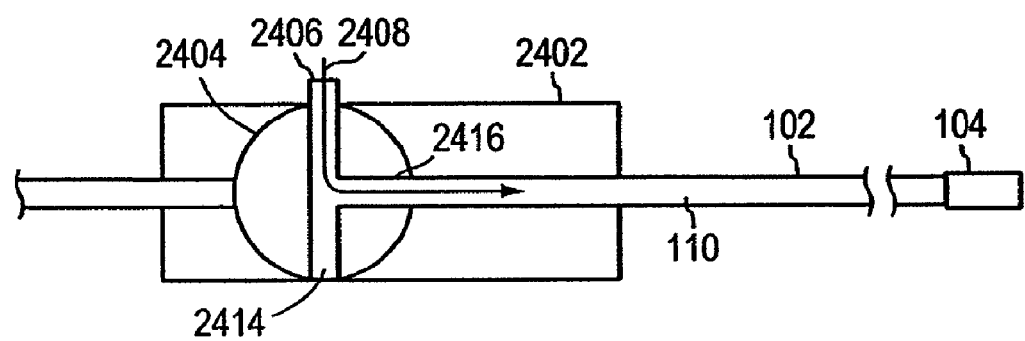
FIGS. 24B and 24C are illustrative cross sectional diagrams of the handle shown in FIG. 24A.
Figure 24C:
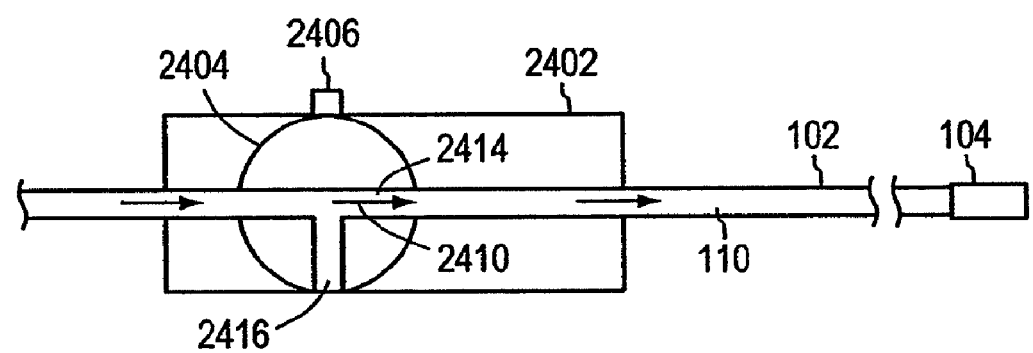

Referring to FIGS. 24A-C, in yet another embodiment, the suction retrieval device 100 can include a handle 2402. The handle 2402 includes a rotatable valve 2404 which is used to enable and disable the suction in the distal portion 106 of the suction passageway 110 by redirecting the suction from the vacuum source. The valve 2404 includes a handle 2412 (for rotating the valve) and two perpendicular suction tubes 2416, 2414. When the valve 2404 is rotated to an open position (FIG. 24B), a suction port 2406 is put in communication with the vacuum source via the suction tubes 2414, 2416. Outside air is pulled through the suction port 2406, through the suction tubes 2414, 2416, and into the suction passageway 100 by a vacuum source as indicated by arrow 2408. The suction in the distal portion 106 of the suction passageway 110 is thereby disabled. When the valve 2404 is rotated to a closed position (FIG. 24C), the suction port 2406 is sealed and the distal portion 106 of the suction passageway 110 is put in communication with the vacuum source via suction tube 2414. The suction in the suction passageway 110 is thereby enabled as indicated by arrows 2410.

Variations, modifications, and other implementations of what is described herein may occur to those of ordinary skill in the art without departing from the spirit and scope of the invention. Accordingly, the invention is not to be defined only by the preceding illustrative description.

What is claimed is:

1. A medical device, comprising:
an elongated member configured to be disposed within a urinary tract of a patient, the elongated member defining a suction passageway along a longitudinal axis of the elongated member, the elongated member having a proximal portion and a distal portion, the proximal portion configured to be coupled to a vacuum source configured to provide suction through the suction passageway,
the distal portion of the elongated member having a tip, the tip including a side wall having an outer surface, a distal end surface, and an inner surface defining a portion of the suction passageway, the side wall between the inner surface and the outer surface being devoid of another lumen, the inner surface being gradually tapered such that an inner diameter of the tip is less than an inner diameter of a portion of the elongated member disposed proximally from the tip, the distal end surface of the side wall configured to contact a kidney stone and retain the kidney stone when the suction is provided through the suction passageway; and
a blocking member coupled to the tip such that a portion of the blocking member extends from the outer surface of the tip, the blocking member configured to contact a portion of the urinary tract of the patient, the blocking member being substantially rigid and having a distal end surface that is substantially co-planar with the distal end surface of the side wall.

2. The medical device of claim 1, wherein a maximum outer diameter of the blocking member is greater than a maximum outer diameter of the tip.

3. The medical device of claim 1, wherein the blocking member configured to prevent tissue proximate the kidney stone from entering the suction passageway when the suction is provided through the suction passageway.

4. The medical device of claim 1, wherein at least a portion of the tip is disposed within a cavity defined by the blocking member.

5. The medical device of claim 1, wherein the elongated member includes a reinforcement configured to help resist collapse of the suction passageway.

6. The medical device of claim 1, wherein the elongated member includes a mesh reinforcement configured to help resist collapse of the suction passageway.

7. The medical device of claim 1, wherein the elongated member includes a coil member.

8. A medical device, comprising:
an elongated member configured to be disposed within a urinary tract of a patient, the elongated member defining a suction passageway along a longitudinal axis of the elongated member, the elongated member having a proximal portion and a distal portion, the proximal portion configured to be coupled to a vacuum source to provide suction through the suction passageway,
the distal portion of the elongated member having a tip, the tip including a side wall having an outer surface and an inner surface defining a portion of the suction passageway, the side wall between the inner surface and the outer surface being devoid of another passageway, the inner surface being gradually tapered such that an inner diameter of the tip is less than an inner diameter of a portion of the elongated member disposed proximally from the tip, the distal end surface of the side wall configured to contact a kidney stone and retain the kidney stone when the suction is provided through the suction passageway; and
a concave member coupled to the tip, the concave member being substantially rigid, the concave member configured to prevent tissue proximate the kidney stone from entering the suction passageway when the suction is provided through the suction passageway, a maximum outer diameter of the concave member is greater than a maximum outer diameter of the tip, the concave member having a distal end surface substantially co-planar with the distal end surface of the side wall.

9. The medical device of claim 8, wherein a portion of the concave member extends radially from the outer surface of the tip.

10. The medical device of claim 8, wherein the elongated member includes a reinforcement configured to help resist collapse of the suction passageway.

11. The medical device of claim 8, wherein the elongated member includes a mesh reinforcement configured to help resist collapse of the suction passageway.

12. The medical device of claim 8, wherein the elongated member includes a coil member.

* * * * *